United States Patent
Denison et al.

(10) Patent No.: US 7,252,675 B2
(45) Date of Patent: Aug. 7, 2007

(54) EMBOLIC FILTERING DEVICES

(75) Inventors: Andy E. Denison, Temecula, CA (US); William J. Harrison, Temecula, CA (US); Benjamin C. Huter, Murrieta, CA (US); Scott J. Huter, Temecula, CA (US); John E. Papp, Temecula, CA (US); Steven T. Saville, Murrieta, CA (US); Kent C. B. Stalker, San Marcos, CA (US)

(73) Assignee: Advanced Cardiovascular, Inc., Santa Clara, CA (US)

(*) Notice: Subject to any disclaimer, the term of this patent is extended or adjusted under 35 U.S.C. 154(b) by 526 days.

(21) Appl. No.: 10/260,710

(22) Filed: Sep. 30, 2002

(65) Prior Publication Data

US 2004/0093009 A1    May 13, 2004

(51) Int. Cl.
*A61M 29/00* (2006.01)
(52) U.S. Cl. .................................... 606/200
(58) Field of Classification Search ............ 606/110, 606/113, 114, 127, 128, 159, 190, 213, 169, 606/170, 198, 200; 604/22
See application file for complete search history.

(56) References Cited

U.S. PATENT DOCUMENTS

| | | |
|---|---|---|
| 3,952,747 A | 4/1976 | Kimmell, Jr. |
| 4,425,908 A | 1/1984 | Simon |
| 4,494,531 A | 1/1985 | Gianturco |
| 4,612,931 A | 9/1986 | Dormia |

(Continued)

FOREIGN PATENT DOCUMENTS

EP    0427429 A3    9/1991

(Continued)

OTHER PUBLICATIONS

Dilitation of the Cartotid Artery By A Temporary Carotid Filter By A. Beck, St. Milic, A.M. Spagnoli, Nov.-Dec. Issue of OPLITAI, An International Journal on Military Medicine and Health Emergencies, pp. 67-74.

*Primary Examiner*—Michael J. Hayes
*Assistant Examiner*—Nguyen Victor
(74) *Attorney, Agent, or Firm*—Fulwider Patton LLP

(57) ABSTRACT

An expandable frame for an embolic filtering device used to capture embolic debris in a body vessel includes a first half frame having a first control arm connected to a second control arm by a partial loop and a second half frame having a first control arm connected to a second control arm by a partial loop. The partial loops cooperatively form a composite loop for attachment of a filtering element which will expand in the body vessel to capture embolic debris entrained in the fluid of the vessel. The lengths and positioning of the first and second control arms of each half frame can be varied to create an expandable frame which conforms to the size and shape of the body vessel in which the filtering device is deployed. Additionally, the radius of the partial loops, along with the length of the arc of the partial loops, can be varied on each of the frames to create a composite filtering assembly that can easily adapt to the size and shape of the body vessel. Additionally, the control arms of the half frames can be disposed either proximally or distally of the composite loop to create a distinct filtering structure.

15 Claims, 10 Drawing Sheets

U.S. PATENT DOCUMENTS

| | | |
|---|---|---|
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,423 A * | 3/1992 | Fearnot ............... 606/159 |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,158,548 A | 10/1992 | Lau et al. |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,776,162 A | 7/1998 | Kleshinski |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maas |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,944,728 A | 8/1999 | Bates |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,042,598 A | 3/2000 | Tsugita et al. |
| 6,053,932 A | 4/2000 | Daniel et al. |
| 6,059,814 A | 5/2000 | Ladd |
| 6,066,158 A | 5/2000 | Engelson et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,117,154 A | 9/2000 | Barbut et al. |
| 6,129,739 A | 10/2000 | Khosravi |
| 6,136,015 A | 10/2000 | Kurz |
| 6,136,016 A | 10/2000 | Barbut et al. |
| 6,142,987 A | 11/2000 | Tsugita |
| 6,152,946 A | 11/2000 | Broome et al. |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita et al. |
| 6,168,604 B1 | 1/2001 | Cano |
| 6,171,327 B1 | 1/2001 | Daniel |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,290,710 B1 | 4/2001 | Mueller et al. |
| 6,224,620 B1 | 5/2001 | Maahs |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,122 B1 | 6/2001 | Tsukernik |
| 6,254,633 B1 | 7/2001 | Pinchuk et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |

| Patent | Date | Inventor |
|---|---|---|
| 6,267,777 B1 | 7/2001 | Bosma et al. |
| 6,270,477 B1 | 8/2001 | Bagaoisan et al. |
| 6,270,513 B1 | 8/2001 | Tsugita et al. |
| 6,273,901 B1 | 8/2001 | Whitcher et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,656 B1 | 9/2001 | Boyle et al. |
| 6,295,989 B1 | 10/2001 | Connors, III |
| 6,306,163 B1 | 10/2001 | Fitz |
| 6,319,242 B1 | 11/2001 | Patterson et al. |
| 6,319,268 B1 | 11/2001 | Ambrisco et al. |
| 6,325,815 B1 | 12/2001 | Kusleika et al. |
| 6,336,934 B1 | 1/2002 | Gilson et al. |
| 6,340,364 B2 | 1/2002 | Kanesaka |
| 6,340,465 B1 | 1/2002 | Hsu et al. |
| 6,346,116 B1 | 2/2002 | Brooks et al. |
| 6,348,056 B1 | 2/2002 | Bates et al. |
| 6,355,051 B1 | 3/2002 | Sisskind et al. |
| 6,361,545 B1 | 3/2002 | Macoviak et al. |
| 6,361,546 B1 | 3/2002 | Khosravi |
| 6,364,895 B1 | 4/2002 | Greenhalgh |
| 6,364,896 B1 | 4/2002 | Addis |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,383,206 B1 | 5/2002 | Gillick et al. |
| 6,384,062 B1 | 5/2002 | Ikeda et al. |
| 6,391,044 B1 | 5/2002 | Yadav et al. |
| 6,394,978 B1 | 5/2002 | Boyle et al. |
| 6,395,014 B1 | 5/2002 | Macoviak et al. |
| 6,398,756 B2 | 6/2002 | Peterson et al. |
| 6,402,771 B1 | 6/2002 | Palmer et al. |
| 6,406,471 B1 | 6/2002 | Jang et al. |
| 6,423,032 B2 | 7/2002 | Parodi |
| 6,423,086 B1 | 7/2002 | Barbut et al. |
| 6,425,909 B1 | 7/2002 | Dieck et al. |
| 6,428,559 B1 | 8/2002 | Johnson |
| 6,432,122 B1 | 8/2002 | Gilson et al. |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma et al. |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,450,989 B2 | 9/2002 | Dubrul et al. |
| 6,458,139 B1 | 10/2002 | Palmer et al. |
| 6,461,370 B1 | 10/2002 | Gray et al. |
| 6,468,291 B2 * | 10/2002 | Bates et al. .................. 606/200 |
| 6,482,222 B1 | 11/2002 | Bruckheimer et al. |
| 6,485,456 B1 | 11/2002 | Kletschka |
| 6,485,497 B2 | 11/2002 | Wensel et al. |
| 6,485,500 B1 | 11/2002 | Kokish et al. |
| 6,485,501 B1 | 11/2002 | Green |
| 6,485,502 B2 | 11/2002 | Don Michael et al. |
| 6,485,507 B1 | 11/2002 | Walak et al. |
| 6,494,895 B2 | 12/2002 | Addis |
| 6,499,487 B1 | 12/2002 | McKenzie et al. |
| 6,500,166 B1 | 12/2002 | Zadno Azizi et al. |
| 6,506,203 B1 | 1/2003 | Boyle et al. |
| 6,506,205 B2 | 1/2003 | Goldberg et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,550 B1 | 2/2003 | Konya et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,530,939 B1 | 3/2003 | Hopkins et al. |
| 6,530,940 B2 | 3/2003 | Fisher |
| 6,533,800 B1 | 3/2003 | Barbut |
| 6,537,294 B1 | 3/2003 | Boyle et al. |
| 6,537,295 B2 | 3/2003 | Petersen |
| 6,537,296 B2 | 3/2003 | Levinson et al. |
| 6,537,297 B2 | 3/2003 | Tsugita et al. |
| 6,540,722 B1 * | 4/2003 | Boyle et al. .................. 604/106 |
| 6,540,767 B1 | 4/2003 | Walak et al. |
| 6,540,768 B1 | 4/2003 | Diaz et al. |
| 6,544,276 B1 | 4/2003 | Azizi |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,268 B1 | 4/2003 | Kaganov et al. |
| 6,551,341 B2 | 4/2003 | Boylan et al. |
| 6,551,342 B1 | 4/2003 | Shen et al. |
| 6,558,401 B1 | 5/2003 | Azizi |
| 6,558,405 B1 | 5/2003 | McInnes |
| 6,562,058 B2 | 5/2003 | Seguin |
| 6,565,591 B2 | 5/2003 | Kelly et al. |
| 6,569,184 B2 | 5/2003 | Huter |
| 6,575,995 B1 | 6/2003 | Huter et al. |
| 6,575,996 B1 * | 6/2003 | Denison et al. .............. 606/200 |
| 6,575,997 B1 | 6/2003 | Palmer et al. |
| 6,582,447 B1 | 6/2003 | Patel et al. |
| 6,582,448 B1 | 6/2003 | Boyle et al. |
| 6,585,756 B1 | 7/2003 | Strecker |
| 6,589,263 B1 | 7/2003 | Hopkins et al. |
| 6,589,265 B1 | 7/2003 | Palmer et al. |
| 6,592,546 B1 | 7/2003 | Barbut et al. |
| 6,592,606 B2 | 7/2003 | Huter et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,599,307 B1 | 7/2003 | Huter et al. |
| 6,599,308 B2 | 7/2003 | Amplatz |
| 6,602,269 B2 | 8/2003 | Wallace et al. |
| 6,602,271 B2 | 8/2003 | Adams et al. |
| 6,602,272 B2 | 8/2003 | Boylan et al. |
| 6,602,273 B2 | 8/2003 | Marshall |
| 6,605,102 B1 | 8/2003 | Mazzocchi et al. |
| 6,605,111 B2 | 8/2003 | Bose et al. |
| 6,607,506 B2 | 8/2003 | Kletschka |
| 6,610,077 B1 | 8/2003 | Hancock et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita et al. |
| 6,620,182 B1 | 9/2003 | Khosravi |
| 6,623,450 B1 | 9/2003 | Dutta |
| 6,629,953 B1 | 10/2003 | Boyd |
| 6,632,236 B2 | 10/2003 | Hogendijk |
| 6,632,241 B1 | 10/2003 | Hancock et al. |
| 6,635,068 B1 | 10/2003 | Dubrul et al. |
| 6,635,070 B2 | 10/2003 | Leeflang et al. |
| 6,638,293 B1 | 10/2003 | Makowner et al. |
| 6,638,294 B1 | 10/2003 | Palmer |
| 6,645,220 B1 | 11/2003 | Huter et al. |
| 6,645,221 B1 | 11/2003 | Richter |
| 6,645,223 B2 | 11/2003 | Boyle et al. |
| 6,645,224 B2 | 11/2003 | Gilson et al. |
| 6,652,480 B1 | 11/2003 | Imran et al. |
| 6,652,505 B1 | 11/2003 | Tsugita et al. |
| 6,652,554 B1 | 11/2003 | Wholey et al. |
| 6,652,557 B1 | 11/2003 | MacDonald |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |

| Patent No. | Date | Inventor |
|---|---|---|
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,673,090 B2 | 1/2004 | Root et al. |
| 6,676,666 B2 | 1/2004 | Vrba et al. |
| 6,676,682 B1 | 1/2004 | Tsugita et al. |
| 6,676,683 B1 | 1/2004 | Addis |
| 6,679,902 B1 | 1/2004 | Boyle et al. |
| 6,679,903 B2 | 1/2004 | Kurz |
| 6,682,546 B2 | 1/2004 | Amplatz |
| 6,685,722 B1 | 2/2004 | Rosenbluth et al. |
| 6,689,151 B2 | 2/2004 | Becker et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,695,864 B2 | 2/2004 | Macoviak et al. |
| 6,696,666 B2 | 2/2004 | Merdan et al. |
| 6,699,260 B2 | 3/2004 | Dubrul et al. |
| 6,702,834 B1 | 3/2004 | Boyle et al. |
| 6,706,055 B2 | 3/2004 | Douk et al. |
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha et al. |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salahieh et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan |
| 6,902,540 B2 | 6/2005 | Dorros et al. |
| 6,908,474 B2 | 6/2005 | Hogendijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah |
| 6,964,672 B2 | 11/2005 | Brady |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo |
| 6,979,344 B2 | 12/2005 | Jones et al. |
| 6,986,778 B2 | 1/2006 | Zadno-Azizi |
| 6,989,019 B2 | 1/2006 | Mazzocchi et al. |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Petersen |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazzocchi et al. |
| 7,037,320 B2 | 5/2006 | Brady et al. |
| 7,041,116 B2 | 5/2006 | Goto et al. |
| 7,044,958 B2 | 5/2006 | Douk et al. |
| 7,048,752 B2 | 5/2006 | Mazzocchi |
| 7,048,758 B2 | 5/2006 | Boyle et al. |
| 7,056,328 B2 | 6/2006 | Arnott |
| 7,060,082 B2 | 6/2006 | Goll et al. |
| 7,077,854 B2 | 7/2006 | Khosravi |
| 7,094,243 B2 | 8/2006 | Mulholland |
| 7,094,249 B1 | 8/2006 | Broome et al. |
| 7,097,440 B2 | 8/2006 | Papp et al. |
| 7,097,651 B2 | 8/2006 | Harrison et al. |
| 7,101,379 B2 | 9/2006 | Gregory, Jr et al. |
| 7,101,380 B2 | 9/2006 | Khachin et al. |
| 7,108,707 B2 | 9/2006 | Huter et al. |
| 2002/0026203 A1 | 2/2002 | Bates et al. |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0095171 A1 | 7/2002 | Belef |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kuskeika et al. |
| 2002/0111659 A1 | 8/2002 | Russo et al. |
| 2002/0115942 A1 | 8/2002 | Stanford et al. |
| 2002/0120286 A1 | 8/2002 | Dobrava et al. |
| 2002/0120287 A1 | 8/2002 | Huter |

| | | | | | | |
|---|---|---|---|---|---|---|
| 2002/0121472 A1 | 9/2002 | Garner et al. | | 2003/0135162 A1 | 7/2003 | Deyette, Jr. et al. |
| 2002/0123720 A1 | 9/2002 | Kusleika et al. | | 2003/0135232 A1 | 7/2003 | Douk et al. |
| 2002/0123755 A1 | 9/2002 | Lowe et al. | | 2003/0139764 A1 | 7/2003 | Levinson et al. |
| 2002/0128679 A1 | 9/2002 | Turovskiy et al. | | 2003/0144685 A1 | 7/2003 | Boyle et al. |
| 2002/0128680 A1 | 9/2002 | Pavlovic | | 2003/0144689 A1 | 7/2003 | Brady et al. |
| 2002/0128681 A1 | 9/2002 | Broome et al. | | 2003/0150821 A1 | 8/2003 | Bates et al. |
| 2002/0133092 A1 | 9/2002 | Oslund et al. | | 2003/0153935 A1 | 8/2003 | Mialhe |
| 2002/0138094 A1 | 9/2002 | Borilla et al. | | 2003/0153942 A1 | 8/2003 | Wang et al. |
| 2002/0138095 A1 | 9/2002 | Mazzocchi et al. | | 2003/0153943 A1 | 8/2003 | Michael et al. |
| 2002/0143360 A1 | 10/2002 | Douk et al. | | 2003/0158574 A1 | 8/2003 | Esch et al. |
| 2002/0143361 A1 | 10/2002 | Douk et al. | | 2003/0163064 A1 | 8/2003 | Vrba et al. |
| 2002/0151927 A1 | 10/2002 | Douk et al. | | 2003/0171770 A1 | 9/2003 | Anderson et al. |
| 2002/0156456 A1 | 10/2002 | Fisher | | 2003/0171771 A1 | 9/2003 | Shimon |
| 2002/0156457 A1 | 10/2002 | Fisher | | 2003/0171803 A1 | 9/2003 | Berrada et al. |
| 2002/0160395 A1 | 10/2002 | Douk et al. | | 2003/0176884 A1 | 9/2003 | Broome et al. |
| 2002/0161390 A1 | 10/2002 | Mouw | | 2003/0176885 A1 | 9/2003 | Wholey et al. |
| 2002/0161392 A1 | 10/2002 | Dubrul | | 2003/0176886 A1 | 9/2003 | Sutton et al. |
| 2002/0161393 A1 | 10/2002 | Desmond et al. | | 2003/0176889 A1 | 9/2003 | Boyle et al. |
| 2002/0165576 A1 | 11/2002 | Boyle et al. | | 2003/0181942 A1 | 9/2003 | Daniel et al. |
| 2002/0169414 A1 | 11/2002 | Kletschka | | 2003/0181943 A1 | 9/2003 | Daniel et al. |
| 2002/0169458 A1 | 11/2002 | Connors, III | | 2003/0187474 A1 | 10/2003 | Keegan et al. |
| 2002/0169472 A1 | 11/2002 | Douk et al. | | 2003/0187475 A1 | 10/2003 | Tsugita et al. |
| 2002/0169474 A1 | 11/2002 | Kusleika et al. | | 2003/0187495 A1 | 10/2003 | Cully et al. |
| 2002/0173815 A1 | 11/2002 | Hogendijk et al. | | 2003/0191493 A1 | 10/2003 | Epstein et al. |
| 2002/0173817 A1 | 11/2002 | Kletschka et al. | | 2003/0195554 A1 | 10/2003 | Shen et al. |
| 2002/0188313 A1 | 12/2002 | Johnson et al. | | 2003/0195555 A1 | 10/2003 | Khairkhahan et al. |
| 2002/0188314 A1 | 12/2002 | Anderson et al. | | 2003/0195556 A1 | 10/2003 | Stack et al. |
| 2002/0193825 A1 | 12/2002 | McGuckin et al. | | 2003/0199819 A1 | 10/2003 | Beck |
| 2002/0193826 A1 | 12/2002 | McGuckin et al. | | 2003/0199921 A1 | 10/2003 | Palmer et al. |
| 2002/0193827 A1 | 12/2002 | McGuckin et al. | | 2003/0204168 A1 | 10/2003 | Bosme et al. |
| 2002/0193828 A1 | 12/2002 | Griffin et al. | | 2003/0204202 A1 | 10/2003 | Palmer et al. |
| 2003/0004536 A1 | 1/2003 | Boylan et al. | | 2003/0208222 A1 | 11/2003 | Zadno-Azizi |
| 2003/0004537 A1 | 1/2003 | Boyle et al. | | 2003/0208224 A1 | 11/2003 | Broome |
| 2003/0004539 A1 | 1/2003 | Linder et al. | | 2003/0208225 A1 | 11/2003 | Goll et al. |
| 2003/0004540 A1 | 1/2003 | Linder et al. | | 2003/0208226 A1 | 11/2003 | Bruckheimer et al. |
| 2003/0004541 A1 | 1/2003 | Linder et al. | | 2003/0208227 A1 | 11/2003 | Thomas |
| 2003/0009188 A1 | 1/2003 | Linder et al. | | 2003/0208228 A1 | 11/2003 | Gilson et al. |
| 2003/0009189 A1 | 1/2003 | Gilson et al. | | 2003/0208229 A1 | 11/2003 | Kletschka |
| 2003/0015206 A1 | 1/2003 | Roth et al. | | 2003/0212361 A1 | 11/2003 | Boyle et al. |
| 2003/0018355 A1 | 1/2003 | Roth et al. | | 2003/0212429 A1 | 11/2003 | Keegan et al. |
| 2003/0023265 A1 | 1/2003 | Forber | | 2003/0212431 A1 | 11/2003 | Brady et al. |
| 2003/0028238 A1 | 2/2003 | Burkett et al. | | 2003/0212434 A1 | 11/2003 | Thielen |
| 2003/0032941 A1 | 2/2003 | Boyle et al. | | 2003/0216774 A1 | 11/2003 | Larson |
| 2003/0032977 A1 | 2/2003 | Brady et al. | | 2003/0220665 A1 | 11/2003 | Eskuri et al. |
| 2003/0040770 A1 | 2/2003 | Hyodoh et al. | | 2003/0225418 A1 | 12/2003 | Eskuri et a. |
| 2003/0042186 A1 | 3/2003 | Boyle et al. | | 2003/0225435 A1 | 12/2003 | Huter et al. |
| 2003/0045898 A1 | 3/2003 | Harrison et al. | | 2003/0229295 A1 | 12/2003 | Houde et al. |
| 2003/0057156 A1 | 3/2003 | Peterson et al. | | 2003/0229374 A1 | 12/2003 | Brady et al. |
| 2003/0060782 A1 | 3/2003 | Bose et al. | | 2003/0233117 A1 | 12/2003 | Adams et al. |
| 2003/0060843 A1 | 3/2003 | Boucher | | 2003/0236545 A1 | 12/2003 | Gilson |
| 2003/0060844 A1 | 3/2003 | Borillo et al. | | 2004/0002730 A1 | 1/2004 | Denison et al. |
| 2003/0065354 A1 | 4/2003 | Boyle et al. | | 2004/0006361 A1 | 1/2004 | Boyle et al. |
| 2003/0069596 A1 | 4/2003 | Eskuri | | 2004/0006364 A1 | 1/2004 | Ladd |
| 2003/0069597 A1 | 4/2003 | Petersen | | 2004/0006365 A1 | 1/2004 | Brady et al. |
| 2003/0078519 A1 | 4/2003 | Salahieh et al. | | 2004/0006366 A1 | 1/2004 | Huter et al. |
| 2003/0078614 A1 | 4/2003 | Satahieh et al. | | 2004/0006367 A1 | 1/2004 | Johnson et al. |
| 2003/0083692 A1 | 5/2003 | Vrba et al. | | 2004/0006368 A1 | 1/2004 | Mazzocchi et al. |
| 2003/0083693 A1 | 5/2003 | Daniel et al. | | 2004/0015184 A1 | 1/2004 | Boyle et al. |
| 2003/0100917 A1 | 5/2003 | Boyle et al. | | 2004/0019363 A1 | 1/2004 | Hanson et al. |
| 2003/0100918 A1 | 5/2003 | Duane | | 2004/0034385 A1 | 2/2004 | Gilson et al. |
| 2003/0105484 A1 | 6/2003 | Boyle et al. | | 2004/0039411 A1 | 2/2004 | Gilson et al. |
| 2003/0109824 A1 | 6/2003 | Anderson et al. | | 2004/0044359 A1 | 3/2004 | Renati et al. |
| 2003/0114879 A1 | 6/2003 | Euteneuer et al. | | 2004/0044360 A1 | 3/2004 | Lowe |
| 2003/0114880 A1 | 6/2003 | Hansen et al. | | 2004/0049226 A1 | 3/2004 | Keegan et al. |
| 2003/0120303 A1 | 6/2003 | Boyle et al. | | 2004/0059372 A1 | 3/2004 | Tsugita |
| 2003/0130680 A1 | 7/2003 | Russell | | 2004/0059373 A1 | 3/2004 | Shapiro et al. |
| 2003/0130681 A1 | 7/2003 | Ungs | | 2004/0082697 A1 | 4/2004 | Broome et al. |
| 2003/0130682 A1 | 7/2003 | Broome et al. | | 2004/0082968 A1 | 4/2004 | Krolik et al. |
| 2003/0130684 A1 | 7/2003 | Brady et al. | | 2004/0088000 A1 | 5/2004 | Muller |
| 2003/0130685 A1 | 7/2003 | Daniel et al. | | 2004/0088002 A1 | 5/2004 | Boyle et al. |
| 2003/0130686 A1 | 7/2003 | Daniel et al. | | 2004/0093009 A1 | 5/2004 | Denison et al. |
| 2003/0130687 A1 | 7/2003 | Daniel et al. | | 2004/0093010 A1 | 5/2004 | Gesswein et al. |
| 2003/0130688 A1 | 7/2003 | Daniel et al. | | 2004/0093011 A1 | 5/2004 | Vrba |

| | | | | | |
|---|---|---|---|---|---|
| 2004/0093012 A1 | 5/2004 | Cully et al. | 2005/0101987 A1 | 5/2005 | Salahich |
| 2004/0093013 A1 | 5/2004 | Brady et al. | 2005/0101988 A1 | 5/2005 | Stanford et al. |
| 2004/0098022 A1 | 5/2004 | Barone | 2005/0101989 A1 | 5/2005 | Cully et al. |
| 2004/0098026 A1 | 5/2004 | Joergensen et al. | 2005/0113865 A1 | 5/2005 | Daniel et al. |
| 2004/0098032 A1 | 5/2004 | Papp et al. | 2005/0119688 A1 | 6/2005 | Bergheim |
| 2004/0098033 A1 | 5/2004 | Leeflang et al. | 2005/0119689 A1 | 6/2005 | Mazzocchi et al. |
| 2004/0102806 A1 | 5/2004 | Broome et al. | 2005/0119690 A1 | 6/2005 | Mazzocchi et al. |
| 2004/0102807 A1 | 5/2004 | Kusleika et al. | 2005/0119691 A1 | 6/2005 | Daniel et al. |
| 2004/0106944 A1 | 6/2004 | Daniel et al. | 2005/0124931 A1 | 6/2005 | Fulton et al. |
| 2004/0111111 A1 | 6/2004 | Lin | 2005/0125023 A1 | 6/2005 | Bates et al. |
| 2004/0116960 A1 | 6/2004 | Demond et al. | 2005/0131450 A1 | 6/2005 | Nicholson et al. |
| 2004/0122466 A1 | 6/2004 | Bales | 2005/0131453 A1 | 6/2005 | Parodi |
| 2004/0127933 A1 | 7/2004 | Demond et al. | 2005/0149110 A1 | 7/2005 | Wholey et al. |
| 2004/0127934 A1 | 7/2004 | Gilson et al. | 2005/0149112 A1 | 7/2005 | Barbut |
| 2004/0127936 A1 | 7/2004 | Salaheih et al. | 2005/0149113 A1 | 7/2005 | Douk et al. |
| 2004/0138693 A1 | 7/2004 | Eskuri et al. | 2005/0159772 A1 | 7/2005 | Lowe et al. |
| 2004/0138694 A1 | 7/2004 | Tran et al. | 2005/0159773 A1 | 7/2005 | Broome et al. |
| 2004/0138696 A1 | 7/2004 | Drasler et al. | 2005/0159774 A1 | 7/2005 | Belef |
| 2004/0147955 A1 | 7/2004 | Beulke et al. | 2005/0171573 A1 | 8/2005 | Salaheih et al. |
| 2004/0153118 A1 | 8/2004 | Clubb et al. | 2005/0177187 A1 | 8/2005 | Gray et al. |
| 2004/0153119 A1 | 8/2004 | Kusleika et al. | 2005/0182440 A1 | 8/2005 | Bates et al. |
| 2004/0158275 A1 | 8/2004 | Crank et al. | 2005/0182441 A1 | 8/2005 | Denison et al. |
| 2004/0158277 A1 | 8/2004 | Lowe et al. | 2005/0192623 A1 | 9/2005 | Mazzocchi et al. |
| 2004/0158278 A1 | 8/2004 | Becker et al. | 2005/0192624 A1 | 9/2005 | Mazzocchi et al. |
| 2004/0158279 A1 | 8/2004 | Petersen | 2005/0203567 A1 | 9/2005 | Linder atl. |
| 2004/0158280 A1 | 8/2004 | Morris et al. | 2005/0203568 A1 | 9/2005 | Burg et al. |
| 2004/0158281 A1 | 8/2004 | Boylan et al. | 2005/0203569 A1 | 9/2005 | Kusleika et al. |
| 2004/0167564 A1 | 8/2004 | Fedie | 2005/0203570 A1 | 9/2005 | Mazzocchi et al. |
| 2004/0167565 A1 | 8/2004 | Beulke et al. | 2005/0203571 A1 | 9/2005 | Maxxocchi et al. |
| 2004/0167566 A1 | 8/2004 | Beulke et al. | 2005/0209634 A1 | 9/2005 | Brady et al. |
| 2004/0167567 A1 | 8/2004 | Cano et al. | 2005/0209635 A1 | 9/2005 | Gilson et al. |
| 2004/0167568 A1 | 8/2004 | Boylan et al. | 2005/0216051 A1 | 9/2005 | Mazzocchi et al. |
| 2004/0172055 A1 | 9/2004 | Huter et al. | 2005/0216052 A1 | 9/2005 | Mazzocchi et al. |
| 2004/0176794 A1 | 9/2004 | Khosravi | 2005/0216053 A1 | 9/2005 | Douk et al. |
| 2004/0193208 A1 | 9/2004 | Talpade et al. | 2005/0222583 A1 | 10/2005 | Cano et al. |
| 2004/0199198 A1 | 10/2004 | Beulke et al. | 2005/0222604 A1 | 10/2005 | Schaeffer et al. |
| 2004/0199199 A1 | 10/2004 | Krolik et al. | 2005/0222607 A1 | 10/2005 | Palmer et al. |
| 2004/0199203 A1 | 10/2004 | Oslund et al. | 2005/0228437 A1 | 10/2005 | Gilson et al. |
| 2004/0204737 A1 | 10/2004 | Boismier et al. | 2005/0228438 A1 | 10/2005 | Sachar et al. |
| 2004/0210250 A1 | 10/2004 | Eskuri | 2005/0228439 A1 | 10/2005 | Andrews et al. |
| 2004/0220608 A1 | 11/2004 | D'Aquanni et al. | 2005/0234502 A1 | 10/2005 | Gilson et al. |
| 2004/0220609 A1 | 11/2004 | Douk et al. | 2005/0240215 A1 | 10/2005 | Ellis |
| 2004/0220611 A1 | 11/2004 | Ogle | 2005/0245866 A1 | 11/2005 | Azizi |
| 2004/0225321 A1 | 11/2004 | Krolik et al. | 2005/0267517 A1 | 12/2005 | Ungs |
| 2004/0225322 A1 | 11/2004 | Garrison et al. | 2005/0283184 A1 | 12/2005 | Gilson et al. |
| 2004/0236368 A1 | 11/2004 | McGucklin, Jr. et al. | 2005/0283185 A1 | 12/2005 | Linder et al. |
| 2004/0236369 A1 | 11/2004 | Dubrul | 2005/0283186 A1 | 12/2005 | Berrada et al. |
| 2004/0249409 A1 | 12/2004 | Krolik et al. | 2005/0288705 A1 | 12/2005 | Gilson et al. |
| 2004/0254601 A1 | 12/2004 | Eskuri | 2006/0004403 A1 | 1/2006 | Gilson et al. |
| 2004/0254602 A1 | 12/2004 | Lehe et al. | 2006/0004405 A1 | 1/2006 | Salaheih et al. |
| 2004/0260308 A1 | 12/2004 | Gilson et al. | 2006/0015138 A1 | 1/2006 | Gertner et al. |
| 2004/0260333 A1 | 12/2004 | Dubrul et al. | 2006/0015139 A1 | 1/2006 | Tsugita et al. |
| 2004/0267301 A1 | 12/2004 | Boylan et al. | 2006/0015140 A1 | 1/2006 | Tsugita et al. |
| 2004/0267302 A1 | 12/2004 | Gilson et al. | 2006/0015141 A1 | 1/2006 | Linder et al. |
| 2005/0004594 A1 | 1/2005 | Nool et al. | 2006/0020285 A1 | 1/2006 | Niermann |
| 2005/0004595 A1 | 1/2005 | Boyle et al. | 2006/0020286 A1 | 1/2006 | Niermann |
| 2005/0004597 A1 | 1/2005 | McGuckin, Jr. et al. | 2006/0025803 A1 | 2/2006 | Mitelberg et al. |
| 2005/0010245 A1 | 1/2005 | Wasicek | 2006/0025804 A1 | 2/2006 | Krolik et al. |
| 2005/0010246 A1 | 1/2005 | Steeter et al. | 2006/0025805 A1 | 2/2006 | DoBrava et al. |
| 2005/0010247 A1 | 1/2005 | Kusleika et al. | 2006/0030876 A1 | 2/2006 | Peacock, III et al. |
| 2005/0021075 A1 | 1/2005 | Bonnette et al. | 2006/0030877 A1 | 2/2006 | Martinez et al. |
| 2005/0021076 A1 | 1/2005 | Mazzocchi et al. | 2006/0030878 A1 | 2/2006 | Anderson et al. |
| 2005/0055048 A1 | 3/2005 | Dieck et al. | 2006/0052817 A1 | 3/2006 | Russo et al. |
| 2005/0070953 A1 | 3/2005 | Riley | 2006/0074446 A1 | 4/2006 | Gilson et al. |
| 2005/0075663 A1 | 4/2005 | Boyle et al. | 2006/0095069 A1 | 5/2006 | Shah et al. |
| 2005/0080446 A1 | 4/2005 | Gilson et al. | 2006/0100659 A1 | 5/2006 | Dinh et al. |
| 2005/0085842 A1 | 4/2005 | Eversull et al. | 2006/0100662 A1 | 5/2006 | Daniel et al. |
| 2005/0090845 A1 | 4/2005 | Boyd | 2006/0100663 A1 | 5/2006 | Palmer et al. |
| 2005/0090857 A1 | 4/2005 | Kusleika et al. | 2006/0116715 A1 | 6/2006 | Khosravi et al. |
| 2005/0090858 A1 | 4/2005 | Pavlovic | 2006/0122643 A1 | 6/2006 | Wasicek |
| 2005/0096691 A1 | 5/2005 | Groothuis et al. | 2006/0122644 A1 | 6/2006 | Brady et al. |
| 2005/0096692 A1 | 5/2005 | Linder et al. | 2006/0122645 A1 | 6/2006 | Brady et al. |
| 2005/0101986 A1 | 5/2005 | Daniel et al. | 2006/0129181 A1 | 6/2006 | Callol et al. |

| | | | |
|---|---|---|---|
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |
| 2006/0184194 A1 | 8/2006 | Pal et al. |
| 2006/0190025 A1 | 8/2006 | Lehe et al. |
| 2006/0195137 A1 | 8/2006 | Sepetka et al. |
| 2006/0195138 A1 | 8/2006 | Goll et al. |
| 2006/0200047 A1 | 9/2006 | Galdonik et al. |
| 2006/0200191 A1 | 9/2006 | Zadno-Azizi |
| 2006/0206139 A1 | 9/2006 | Tekulve |

FOREIGN PATENT DOCUMENTS

| | | |
|---|---|---|
| EP | 0 472 334 A1 | 2/1992 |
| EP | 0533511 A1 | 3/1993 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/23976 | 5/1999 |
| WO | WO99/44510 | 9/1999 |
| WO | WO00/67667 | 11/2000 |
| WO | WO01/10346 | 2/2001 |
| WO | WO01/45592 | 6/2001 |
| WO | WO 01/72205 | 10/2001 |
| WO | WO01/87183 | 11/2004 |

\* cited by examiner

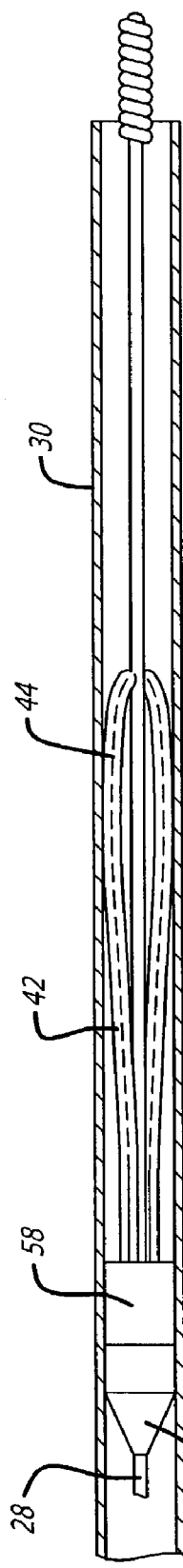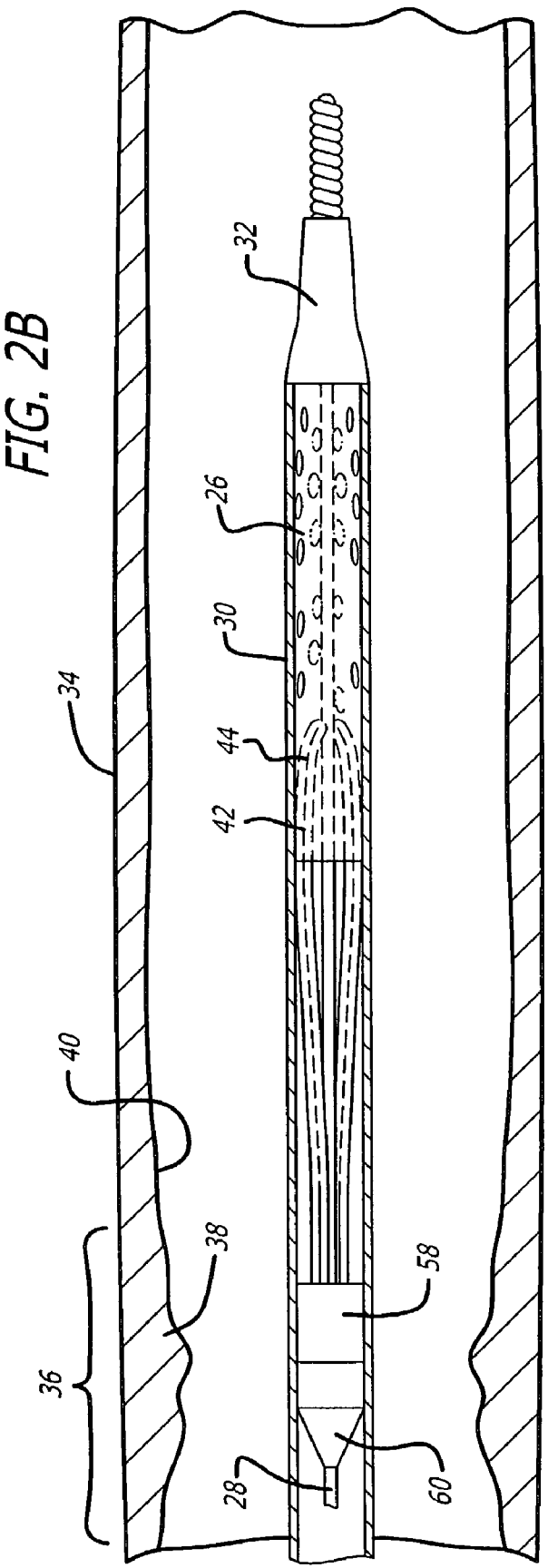
FIG. 2A
FIG. 2B

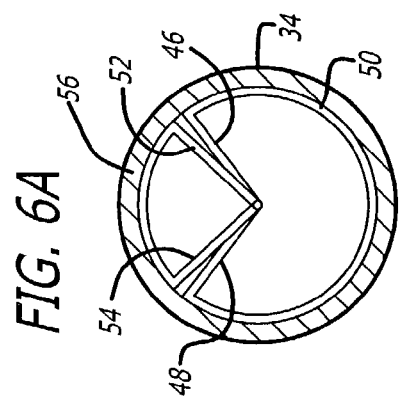
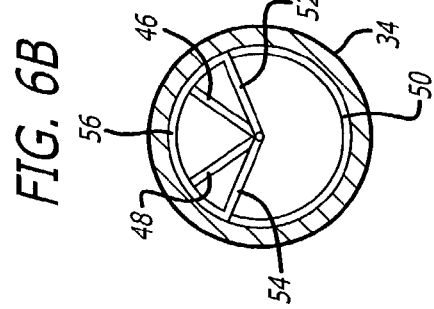
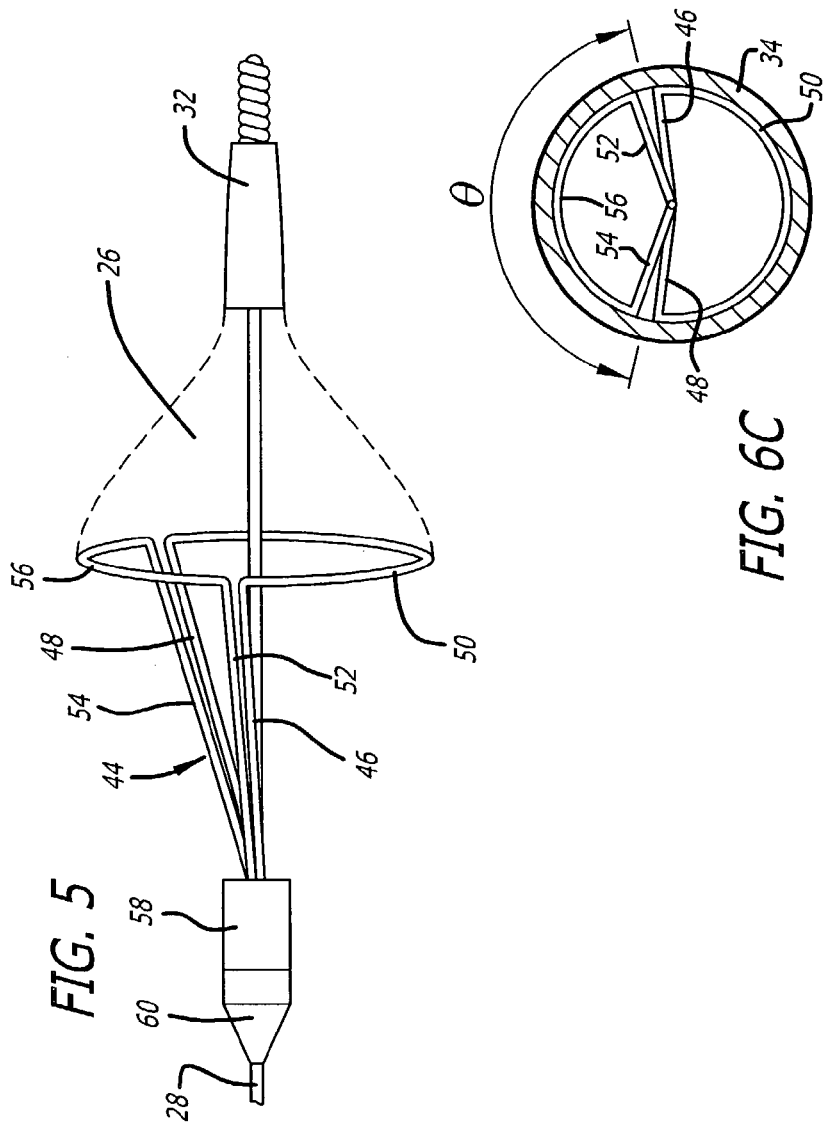
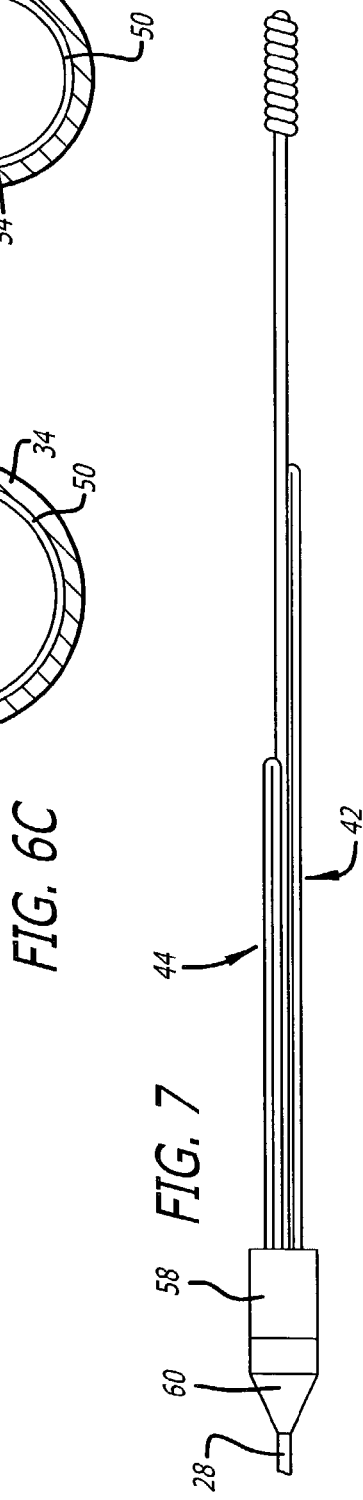

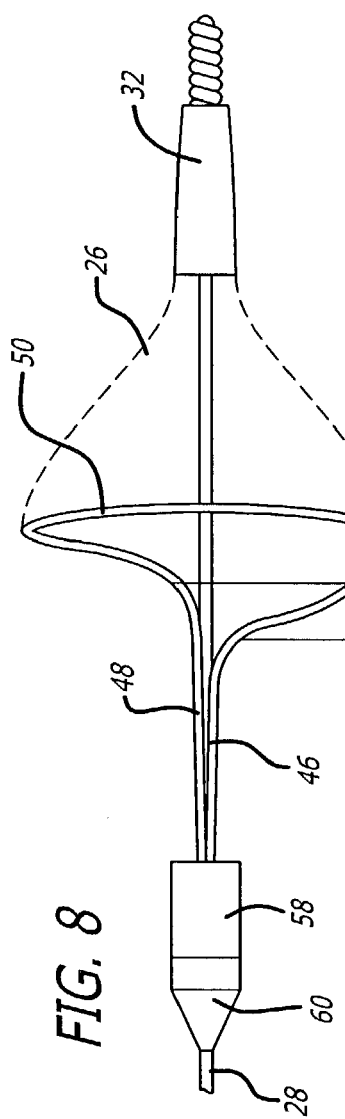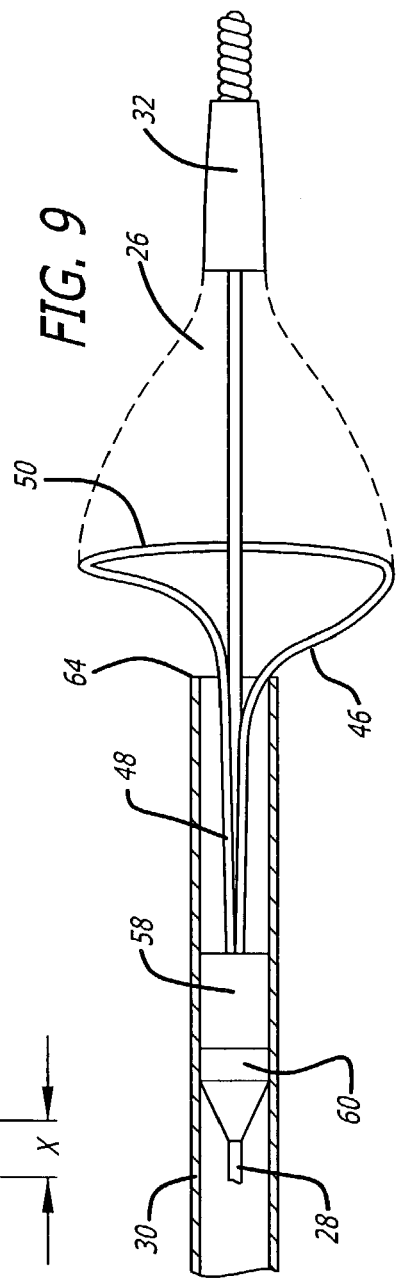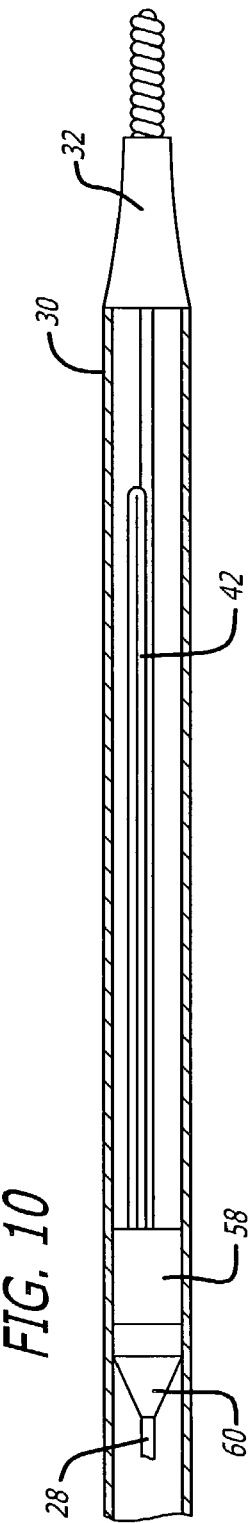

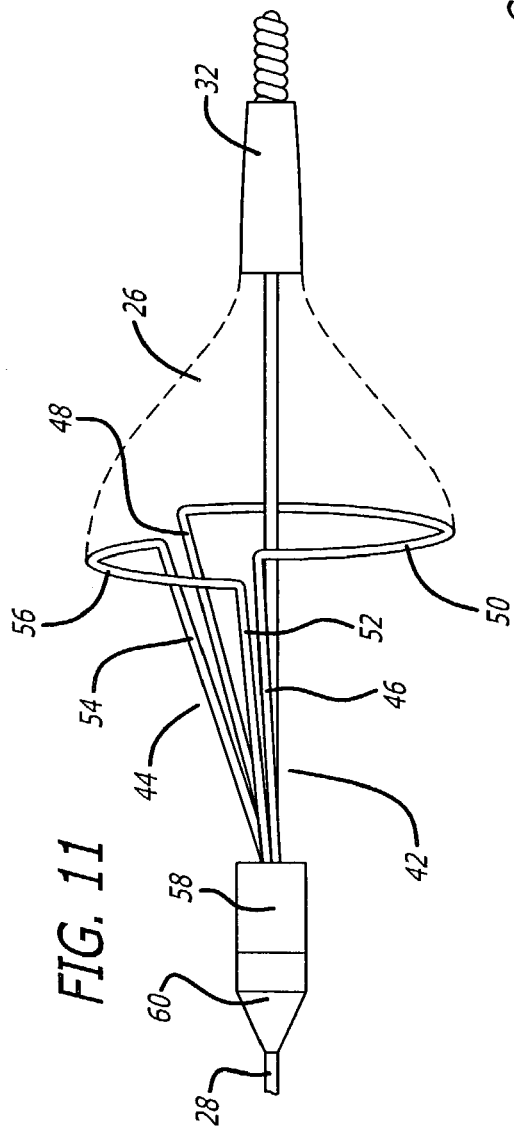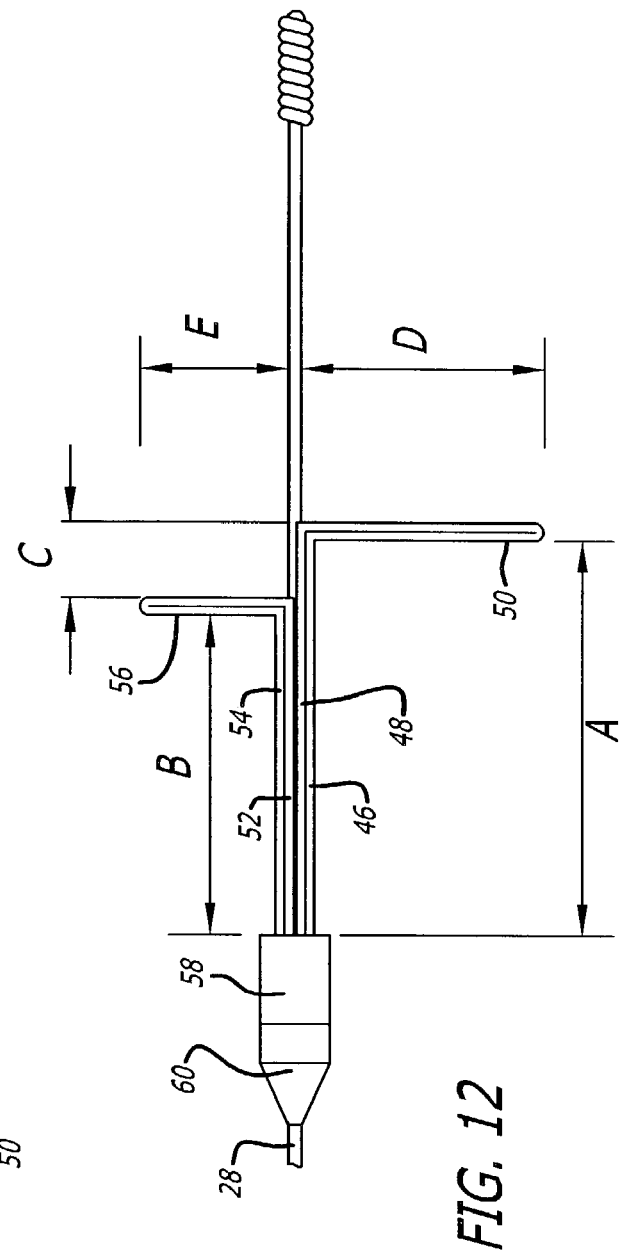

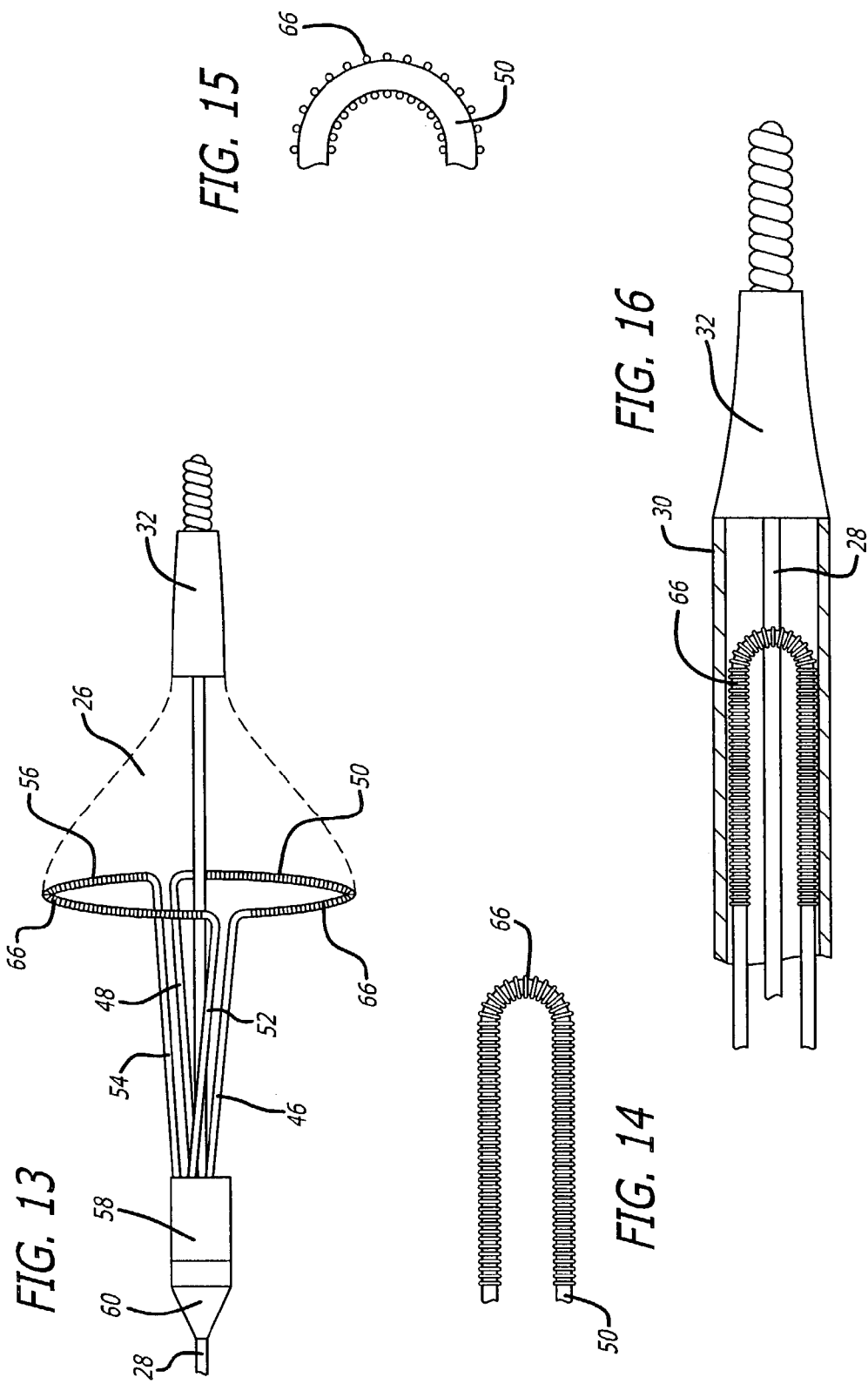

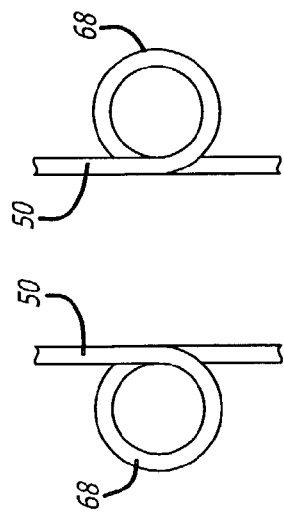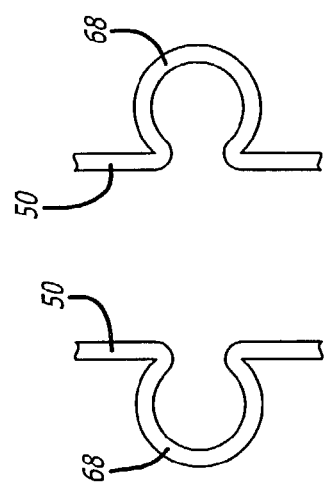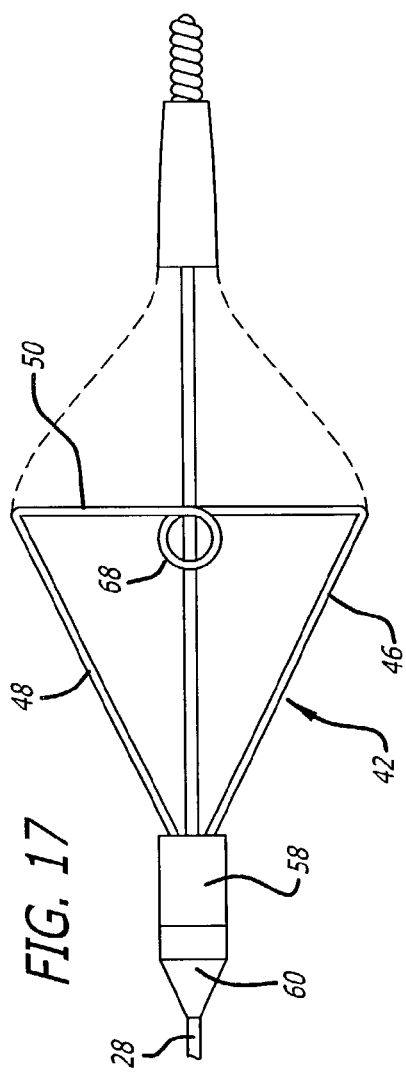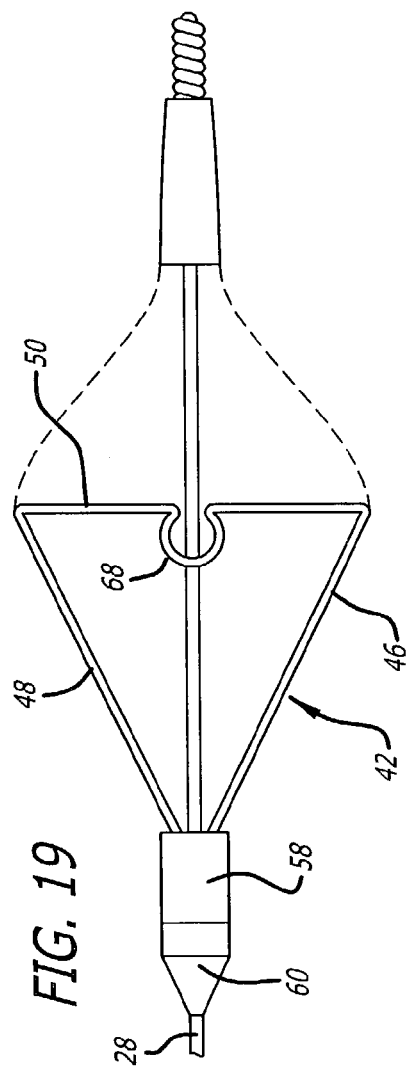

EMBOLIC FILTERING DEVICES

FIELD OF THE INVENTION

The present invention relates generally to filtering devices and systems which can be used when an interventional procedure is being performed in a stenosed or occluded region of a body vessel to capture embolic material that may be created and released into the vessel during the procedure. The present invention is more particularly directed to an embolic filtering device made with a self-expanding frame (also referred to as a basket or cage) having enhanced flexibility and bendability. The present invention is particularly useful when an interventional procedure, such as balloon angioplasty, stenting procedure, laser angioplasty or atherectomy, is being performed in a critical body vessel, such as the carotid arteries, where the release of embolic debris into the bloodstream can occlude the flow of oxygenated blood to the brain, resulting in grave consequences to the patient. While the present invention is particularly useful in carotid procedures, the invention can be used in conjunction with any vascular procedure in which embolic risk is present.

BACKGROUND OF INVENTION

Numerous procedures have been developed for treating occluded blood vessels to allow blood to flow without obstruction. Such procedures usually involve the percutaneous introduction of an interventional device into the lumen of the artery, usually by a catheter. One widely known and medically accepted procedure is balloon angioplasty in which an inflatable balloon is introduced within the stenosed region of the blood vessel to dilate the occluded vessel. The balloon dilatation catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed body vessel in which cutting blades are rotated to shave the deposited plaque from the arterial wall. A catheter is usually used to capture the shaved plaque or thrombus from the bloodstream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque that can travel downstream and lodge somewhere in the patient's vascular system. Pieces of plaque material are sometimes generated during a balloon angioplasty procedure and become released into the bloodstream. Additionally, while complete vaporization of plaque is the intended goal during laser angioplasty, sometimes particles are not fully vaporized and enter the bloodstream. Likewise, not all of the emboli created during an atherectomy procedure may be drawn into the catheter and, as a result, enter the bloodstream as well.

When any of the above-described procedures are performed in the carotid arteries, the release of emboli into the circulatory system can be extremely dangerous and sometimes fatal to the patient. Debris carried by the bloodstream to distal vessels of the brain can cause cerebral vessels to occlude, resulting in a stroke, and in some cases, death. Therefore, although cerebral percutaneous transluminal angioplasty has been performed in the past, the number of procedures performed has been somewhat limited due to the justifiable fear of an embolic stroke occurring should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques include the use of catheters with a vacuum source which provides temporary suction to remove embolic debris from the bloodstream. However, there can be complications associated with such systems if the vacuum catheter does not remove all of the embolic material from the bloodstream. Also, a powerful suction could cause trauma to the patient's vasculature.

Another technique which has had some success utilizes a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self expanding and utilize a restraining sheath which maintains the expandable filter in a collapsed position until it is ready to be expanded within the patient's vasculature. The physician can retract the proximal end of the restraining sheath to expose the expandable filter, causing the filter to expand at the desired location. Once the procedure is completed, the filter can be collapsed, and the filter (with the trapped embolic debris) can then be removed from the vessel. While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the body vessel.

Some prior art expandable filters are attached to the distal end of a guide wire or guide wire-like member which allows the filtering device to be steered in the patient's vasculature as the guide wire is positioned by the physician. Once the guide wire is in proper position in the vasculature, the embolic filter can be deployed to capture embolic debris. The guide wire can then be used by the physician to deliver interventional devices, such as a balloon angioplasty dilatation catheter or a stent delivery catheter, to perform the interventional procedure in the area of treatment. After the procedure is completed, a recovery sheath can be delivered over the guide wire using over-the-wire techniques to collapse the expanded filter for removal from the patient's vasculature.

When a combination of an expandable filter and guide wire is utilized, it is important that the expandable filter portion remains flexible in order to negotiate the often tortuous anatomy through which it is being delivered. An expandable filter which is too stiff could prevent the device from reaching the desired deployment position within the patient's vasculature. As a result, there is a need to increase the flexibility of the expandable filter without compromising its structural integrity once in position within the patient's body vessel. Also, while it is beneficial if the area of treatment is located in a substantially straight portion of the patient's vasculature, sometimes the area of treatment is at a curved portion of the body vessel which can be problematic to the physician when implanting the expandable filter. If the expandable filter portion is too stiff, it is possible that the filter may not fully deploy within the curved portion of the body vessel. As a result, gaps between the filter and vessel wall can be formed which may permit some embolic debris to pass therethrough. Therefore, the filtering device should be sufficiently flexible to be deployed in, and to conform to, a tortuous section of the patient's vasculature, when needed.

Expandable filters can be provided with some increased flexibility by forming the struts of the filter assembly from relatively thin material. However, the use of thin material often can reduce the radiopacity of the expandable filter, often making it difficult for the physician to visualize the filter during deployment. Conversely, the use of thicker materials, which can promote radiopacity of the expandable filter, usually reduces its flexibility, which may impair the deliverability of the expandable filter within the patient.

Another problem presented to a physician utilizing an embolic filtering device is the possible undesired collection of embolic debris on the struts or ribs that form the basket onto which the filter is attached. The exposed surface of proximally located struts provide a potential area where embolic debris can stick, never reaching the filter positioned downstream from these struts. As the embolic filtering device is being collapsed for removal from the patient, it is possible for embolic debris which has become stuck to these struts to become dislodged and enter the blood stream. As a result, the design of the embolic filtering device itself may pose a danger if too many struts are located proximal to the filter since increased surface area will be exposed to the embolic particles. Therefore, it may be beneficial to use thin struts in the proximal region of the filtering device or to reduce the number of struts forming the self-expanding basket.

What has been needed is an expandable filter assembly having high flexibility with sufficient strength and radiopacity to be successfully deployed within a patient's vasculature to collect embolic debris which may be released into the patient's vasculature. The present invention disclosed herein satisfies these and other needs.

SUMMARY OF THE INVENTION

The present invention provides a highly flexible self-expanding frame for use with an embolic filtering device designed to capture embolic debris created during the performance of a therapeutic interventional procedure, such as a balloon angioplasty or stenting procedure, in a body vessel. The present invention provides the physician with an embolic filtering device which is highly flexible to be steered through tortuous anatomy, but yet possesses sufficient strength to hold open a filtering element against the wall of the body vessel for capturing embolic debris. Moreover, the present invention provides sufficient flexibility without compromising the radiopacity characteristics of the filtering device. An embolic filtering device made in accordance with the present invention is relatively easy to deploy and has good flexibility and conformability to the patient's anatomy.

An embolic filter assembly of the present invention utilizes an expandable frame made from a self-expanding material, for example, nickel-titanium (NiTi), and includes a pair of half frames capable of expanding from an unexpanded position having a first delivery diameter to an expanded or deployed position having a second expanded diameter. A filter element made from an embolic-capturing material is attached to the expandable frame to move between the unexpanded position and deployed position.

The half frames which cooperatively form the expandable frame can be set to remain in the expanded, deployed position until an external force is placed over the half frames to collapse and move the frames to the unexpanded position. One way of accomplishing this is through the use of a restraining sheath, for example, which can be placed over the filtering device in a coaxial fashion to contact the half frames and move the half frames into the unexpended position. The embolic filtering device can be implanted in the patient's vasculature and remain implanted for a period of time or can be attached to the distal end of an elongated member, such as a guide wire, for temporary placement in the vasculature. A guide wire may be used in conjunction with the filtering device when embolic debris is to be filtered during an interventional procedure. In this manner, the guide wire and filtering assembly, with the restraining sheath placed over the filter assembly, can be placed into the patient's vasculature. Once the physician properly manipulates the guide wire into the target area, the restraining sheath can be retracted to deploy the expandable frame into the expanded position. This can be easily performed by the physician by simply retracting the proximal end of the restraining sheath (located outside of the patient). Once the restraining sheath is retracted, the self-expanding properties of the frame cause each half frame to move in a outward, radial fashion away from the guide wire to contact the wall of the body vessel. As the half frames expand radially, so does the filter element which will now be maintained in place to collect embolic debris that may be released into the bloodstream as the physician performs the interventional procedure. The guide wire is used by the physician to deliver the necessary interventional device into the area of treatment. The deployed filter element captures any embolic debris created and released into the body vessel during the procedure.

The features of the present invention are primarily directed to the pair of half frames which cooperatively form the expandable frame of the embolic filter assembly. In one aspect of the present invention, the first half frame includes a first control arm connected to a second control arm by a partial loop. The second half frame also includes a first arm connected to a second control arm via a partial loop. The partial loops of this first and second half frames cooperate to form a composite loop to which the filter element can be attached. The partial loops extend radially outward when placed in an expanded position so that a substantially circular loop is created by the two partial loops. In aspect of the present invention, the first control arm of the first half frame has a length which is smaller than the second control arm of the same half frame. Additionally, the length of the first control arm of the second half frame can be smaller than the second control arm of the second half frame. The use of different sized control arms to form each of the first and second half frames creates an offset geometry in the composite loop which can be beneficial when the filter assembly is placed in small diameter body vessels or when deployed on a curved section of a body vessel.

In another aspect of the present invention, the first and second control arms of the first half frame are disposed distally of the composite loop formed by the partial loops. The first and second arms of the second half frame are, in turn, disposed proximally of the composite loop to create diametrically opposed control arms. A third control arm which extends from the partial loop formed on the first half frame is disposed proximally of the composite loop to provide a means for collapsing the first half frame after the half frames have been deployed. This third control arm is designed to contact the distal end of a recovery sheath which is designed to contact the proximally located control arms to cause the half frames to move into the collapsed position for retrieval into the lumen of the recovery sheath. Thereafter, the recovery sheath and filter assembly can be withdrawn from the body vessel.

In another aspect of the present invention, each of the partial loops of the first and second half frames have a particular, circular shaped arc when placed in the expanded position. The arc is generally measured between the point of attachment of the first control arm and the partial loop and the point attachment of the second control arm and the partial loop. In a specific aspect of the present invention, one of the partial loops has a smaller circular-shaped arc than the other partial loop. This allows the smaller circular-shaped arc of the partial loop to move inside the other half frame in that the event the device is placed in an undersized body vessel. As a result, the partial loops of each of the half frames still cooperatively form a circular composite loop which maintains the filter element in contact with the wall of the body vessel. In this manner, the partial loops compensate and readily adapt to the smaller sized vessel.

In other aspects of the present invention, the first and second control arms of the a half basket are set with a shape in the expanded position which prevents the restraining or recovery sheath from retracting both of the control arms at the same time. In this regard, the first control arm, for example, can be set to expand radially outward at a position which is different from the set of the second control arm. Therefore, the end of the restraining sheath initially contacts the first control arm to place a collapsing frame on this control arm, the second control arm has not yet been contacted by the restraining sheath. As the half frame continues to be drawn into the lumen of the recovery sheath, the end of the sheath eventually contacts the second control arm, but at a much later time than it contacts the first control arm, thus providing a staggered collapse of the half frame. This staggered arrangement of the first and second control arm can be implemented with both of the half frames which cooperate to form the expandable frame.

In still other aspects of the present invention, the size of the control arms of one of the half frames can be larger than the length of the control arms of a second half frame. Additionally, the radius of the partial loop of one of the half frames can be different than the radius of the corresponding half frame. As a result, the composite expandable frame can prove to provide beneficial deployment characteristics when implanted, for example, on a curved portion of a body vessel.

The present invention is directed as well to a composite frame formed from two half frames that are attached to a tubular structure that is rotatably mounted to the guide wire. The use of a tubular structure with the half frame design provides a durable embolic filtering assembly that can be rotatably mounted onto a steerable guide wire and will rotate or spin relative to the guide wire once implanted in the body vessel. Such a tubular structure could be utilized in accordance with any of the embodiments shown and described herein.

It is to be understood that the present invention is not limited by the embodiments described herein. The present invention can be used in arteries, veins, and other body vessels. Other features and advantages of the present invention will become more apparent from the following detailed description of the invention, when taken in conjunction with the accompanying exemplary drawings.

BRIEF DESCRIPTION OF THE DRAWINGS

FIG. 2A is an elevational view, partially in cross-section, of the embolic filtering device of FIGS. 1B and 1C as it is restrained within a delivery sheath.

FIG. 2B is an elevational view, partially in cross-section, of the embolic filtering device of FIG. 1A as it is being delivered within a body vessel.

FIG. 5 is a side view of another embodiment of an embolic filtering device embodying features of the present invention.

FIG. 6A is a cross-sectional end view showing the embolic filtering device of FIG. 5 implanted within a body vessel.

FIG. 6B is a cross-sectional end view of the embolic filtering device of FIG. 5 implanted within a body vessel which is smaller than the one depicted in FIG. 6A.

FIG. 6C is a cross-sectional end view of an embolic filtering device implanted within a body vessel which shows the range of arc that the partial loop of the half frames can assume in forming a half frame assembly.

FIG. 7 is a side elevational view of the embolic filtering device (without filter element) of FIG. 5 in its collapsed, delivery position.

FIG. 8 is a side view of another embodiment of an embolic filtering device (shown with only a single half frame) embodying features of the present invention.

FIG. 9 is a side elevational view, partially in cross-section, showing the half frame of the embolic filtering device of FIG. 8 as it is initially being retracted into a restraining sheath.

FIG. 10 is a side elevational view, partially in cross-section, showing the embolic filtering device of FIG. 8 in its collapsed, delivery position within a restraining sheath.

FIG. 11 is a side view of another embodiment of an embolic filtering device embodying features of the present invention.

FIG. 12 is a side elevational view of the embolic filtering device of FIG. 11 in its deployed position.

FIG. 13 is a side view of another embodiment of an embolic filtering device embodying features of the present invention.

FIG. 14 is a side elevational view of the radiopaque coils placed on the end of the half frame which forms part of the expandable frame of the embolic filtering device of FIG. 13.

FIG. 15 is a side elevational view showing an alternative placement of the radiopaque coils on a half frame which forms part of the expandable frame of FIG. 13.

FIG. 16 is a side elevational view, partially in cross-section, of the embolic filtering device of FIG. 13 in its collapsed, delivery position within a restraining sheath.

FIG. 17 is a side elevational view of one particular embodiment of a half frame which forms part of the expandable frame of an embolic filtering device and includes a region of articulation.

FIG. 18A is an exploded view of the region of articulation shown in FIG. 17.

FIG. 18B is an exploded view of the region of articulation, similar to that shown in FIG. 18A, with the region or articulation disposed 180° from the region of articulation shown in FIG. 18A.

FIG. 19 is a side elevational view of one particular embodiment of a half frame which forms part of the embolic filtering device and includes a region of articulation.

FIG. 20A is an exploded view of the region of articulation shown in FIG. 19.

FIG. 20B is an exploded view of a region of articulation similar to that shown in FIG. 20A, with the region of articulation disposed 180° from the region of articulation shown in FIG. 20A.

DETAILED DESCRIPTION OF THE PREFERRED EMBODIMENTS

Figure 1A:
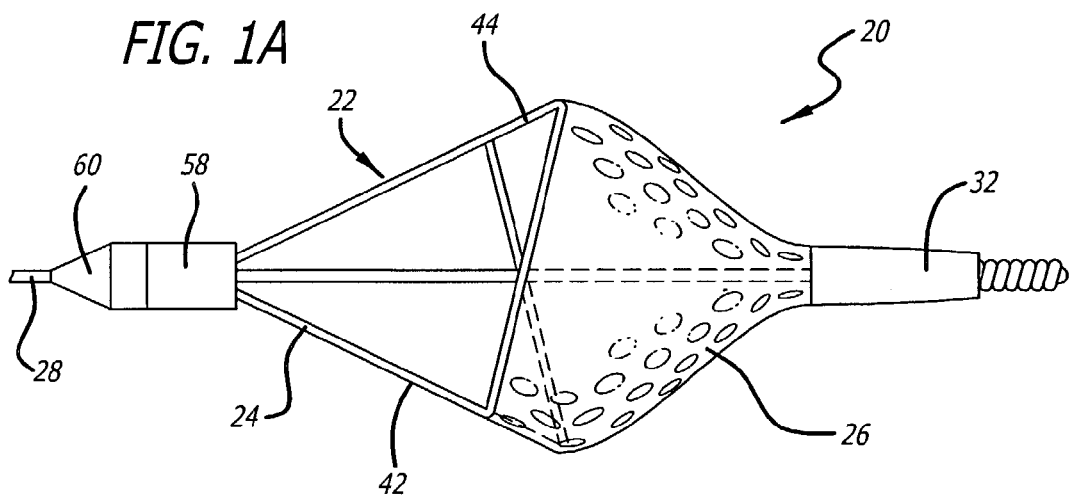
FIG. 1A is a side view of an embolic filtering device embodying features of the present invention.
Figure 1B:
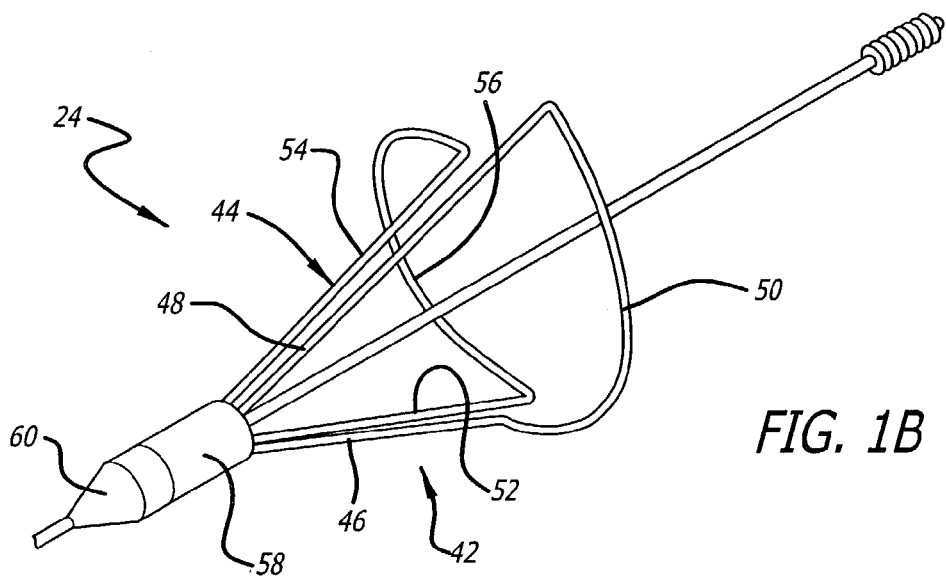
FIG. 1B is a perspective view of the embolic filtering device of FIG. 1A shown without the filter element attached to the expandable frame.
Figure 1C:
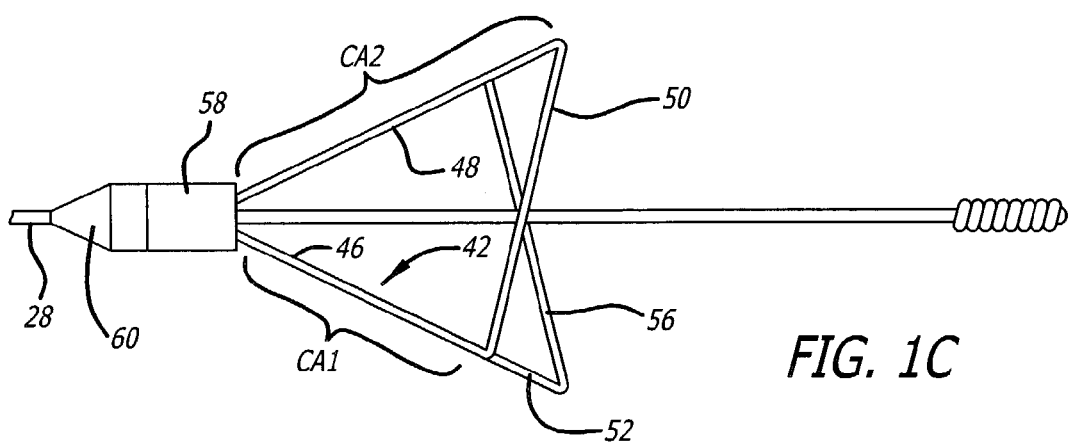
FIG. 1C is a side elevational view of the embolic filtering device of FIG. 1A shown without the filtering element attached to the half frames which form the expandable frame.

Turning now to the drawings, in which like reference numerals represent like or corresponding elements in the drawings, FIGS. 1A, 1B and 1C illustrate one particular embodiment of an embolic filtering device 20 incorporating features of the present invention. This embolic filtering device 20 is designed to capture embolic debris which may be created and released into a body vessel during an interventional procedure. The embolic filtering device 20 includes an expandable filter assembly 22 having a self-expanding frame 24 and a filter element 26 attached thereto. In this particular embodiment, the expandable filter assembly 22 is rotatably mounted on the distal end of an elongated tubular or solid shaft, such as a steerable guide wire 28. A restraining or delivery sheath 30 (see FIGS. 2A–2C) extends coaxially along the guide wire 28 in order to maintain the expandable filter assembly 22 in its unexpanded position until it is ready to be deployed within the patient's vasculature. The expandable filter assembly 22 is deployed by the physician by simply retracting the restraining sheath 30 proximally to expose the expandable filter assembly. Once the restraining sheath is retracted, the self-expanding wire frame 24 becomes uncovered and immediately begins to expand within the body vessel (see FIG. 2C), causing the filter element 26 to expand as well.

An optional obturator 32 affixed to the distal end of the filter assembly 22 can be implemented to prevent possible "snowplowing" of the embolic filtering device as it is being delivered through the vasculature. The obturator can be made from a soft polymeric material, such as Pebax 40D, and preferably has a smooth surface to help the embolic filtering device travel through the vasculature and cross lesions while preventing the distal end of the restraining sheath 30 from "digging" or "snowplowing" into the wall of the body vessel.

Figure 2C:
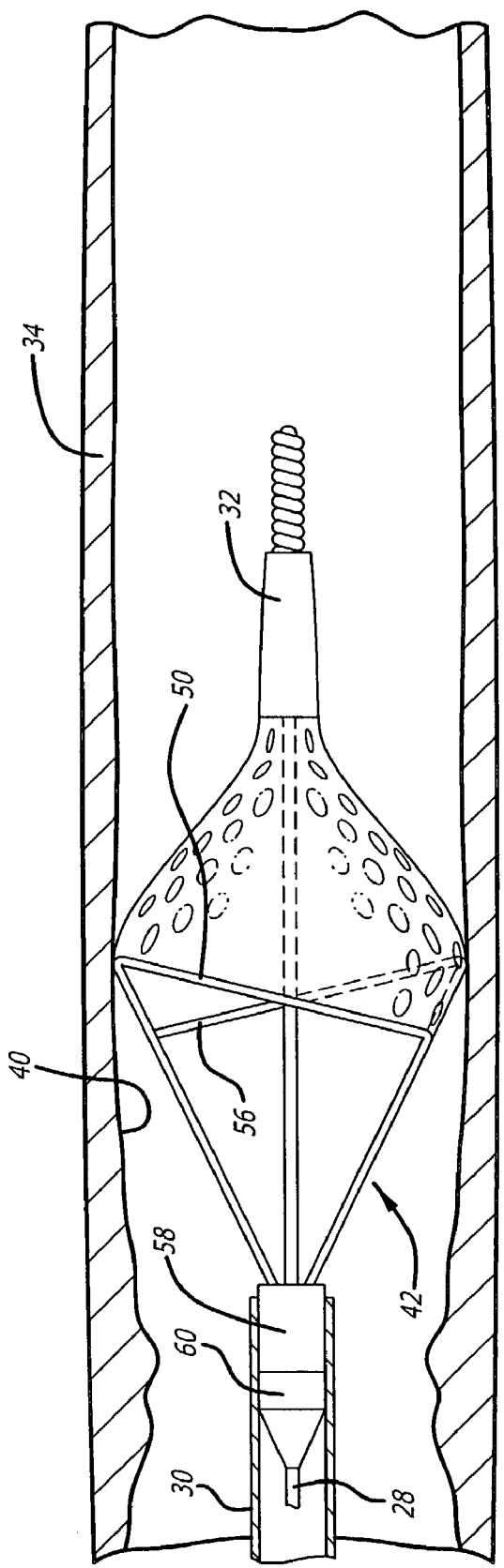
FIG. 2C is an elevational view, partially in cross section, similar to that shown in FIG. 2B, wherein the embolic filtering device is deployed in its expanded, implanted position within the body vessel.

In FIGS. 2B and 2C, the embolic filtering device 20 is shown as it is being delivered within an artery 34 or other body vessel of the patient. Referring now to FIG. 2C, the embolic filtering assembly 22 is shown in its expanded position within the patient's artery 34. This portion of the artery 34 has an area of treatment 36 in which atherosclerotic plaque 38 has built up against the inside wall 40 of the artery 34. The filter assembly 22 is placed distal to, and downstream from, the area of treatment 36. For example, the therapeutic interventional procedure may comprise the implantation of a stent (not shown) to increase the diameter of an occluded artery and increase the flow of blood therethrough. It should be appreciated that the embodiments of the embolic filtering device described herein are illustrated and described by way of example only and not by way of limitation. Also, while the present invention is described in detail as applied to an artery of the patient, those skilled in the art will appreciate that it can also be used in a variety of arteries or other body vessels, such as the coronary arteries, carotid arteries, renal arteries, saphenous vein grafts and other peripheral arteries. Additionally, the present invention can be utilized when a physician performs any one of a number of interventional procedures, such as balloon angioplasty, laser angioplasty or atherectomy which generally require an embolic filtering device to capture embolic debris created during the procedure.

The self-expanding frame 24 includes a pair of half frames 42 and 44 which, upon release from the restraining sheath, expand the filter element 26 into its deployed position within the artery (FIG. 2C). Embolic debris created during the interventional procedure and released into the bloodstream are captured within the deployed filter element 26. Although not shown, a balloon angioplasty catheter can be initially introduced within the patient's vasculature in a conventional SELDINGER technique through a guiding catheter (not shown). The guide wire 28 is disposed through the area of treatment and the dilatation catheter can be advanced over the guide wire 28 within the artery 34 until the balloon portion is directly in the area of treatment 36. The balloon of the dilatation catheter can be expanded, expanding the plaque 38 against the wall 40 of the artery 34 to expand the artery and reduce the blockage in the vessel at the position of the plaque 38. After the dilatation catheter is removed from the patient's vasculature, a stent (not shown) can be implanted in the area of treatment 36 using over-the-wire or rapid exchange techniques to help hold and maintain this portion of the artery 34 and help prevent restenosis from occurring in the area of treatment. The stent could be delivered to the area of treatment on a stent delivery catheter (not shown) which is advanced from the proximal end of the guide wire to the area of treatment. Any embolic debris created during the interventional procedure will be released into the bloodstream and will enter the filter 26. Once the procedure is completed, the interventional device may be removed from the guide wire. The filter assembly 22 can also be collapsed and removed from the artery 34, taking with it any embolic debris trapped within the filter element 26. A recovery sheath (not shown) can be delivered over the guide wire 28 to collapse the filter assembly 22 for removal from the patient's vasculature.

Referring specifically now to FIGS. 1A–1C, the particular embodiment of the frame 24 includes a first half frame 42 and second half frame 44 which cooperatively form a deployment mechanism for expanding the filter element 26 within the patient's vasculature. As can be seen in these figures, the first half frame 42 includes a first control arm 46 and a second control arm 48 connected to each other via a partial loop 50 which extends radially outward once placed in the deployed position as is shown in FIG. 1B. Likewise, the second half frame 44 includes a first control arm 52 and a second control arm 54 connected by a partial loop 56. Once placed in the deployed position as is shown in FIG. 1B, the partial loops 50 and 56 cooperatively form a composite circular shaped loop having a large opening to which the filter element 26 is attached. In this fashion, once the first half frame 42 and the second half frame 44 are deployed, the partial loops 50 and 56 will self-expand radially to contact the wall of the artery to maintain proper wall apposition with the filter element 26. Any embolic debris or unwanted particles which may be entrained in the body fluid passing through the particular body vessel in which the device is implanted should be captured in the filter element.

Each of the first and second control arms of the first half frame 42 and the second half frame 44 are connected to a junction or collar 58 located proximal to the partial loops 50 and 56. In this regard, the ends of each of the first and second control arms are connected substantially together. This junction or collar 58 can be mounted on the guide wire 28 such that the first and second half frames 42 and 44 are rotatably mounted onto the guide wire to allow the guide wire to rotate freely once the first and second half frames 42 and 44 are deployed in the body vessel. In this manner, if the physician should spin the guide wire at its proximal end while placing an interventional device on the guide wire, that rotation will not be transmitted along the guide wire to the deployed wire frame 24. Thus, the frame 24 and the filter element 26 should remain stationary in the event of accidental or intentional rotation of the guide wire at its proximal end. The junction or collar 58 may be disposed between a pair of stop fittings 60, only one of which is shown in FIGS. 1A–1C. The stop fittings provide an abutting shoulder against which the collar 58 can be placed between to allow rotation of the guide wire relative to the frame 24 and to prevent longitudinal motion of the filtering assembly 22 along the guide wire 28. Alternatively, the stop fittings can be positioned a distance away from each other to allow at least some limited range of longitudinal motion of the frame 24 and filter 26 along the guide wire. In this manner, the collar 58 would be disposed between the spaced apart stop fittings to allow both rotation and a limited amount of longitudinal motion of the filtering assembly 22 relative to the guide wire.

Referring specifically again to FIGS. 1A–1C, the particular lengths of the first and second control arms on each of the first and second half frames 42 and 44 are shown and described in greater detail. As can be seen particularly in FIG. 1C, the first half frame 42 has a first control arm 46 having a length which is shorter than the length of the second control arm 48. The length of the control arms are generally measured from the end of the arm as it is mounted to the collar 58 to the transition area where the partial loop 50 starts to extend radially away from the arms once placed in the deployed position. Referring specifically to FIG. 1C, the length of the first control arm 46 is designated by the bracket labeled CA1 and the length of the second control arm 48 is designated by the bracket labeled CA2. In this manner, the first half frame 42 has control arms of unequal length which can be useful when placing the composite filtering device in curved portions of the anatomy. Likewise, the second half frame 44 has a first control arm 52 which is greater in length than the second control arm 54. As a result, as the composite frame 24 is expanded into its deployed position, the differences in the lengths of these control arms formed on the first and second half frames 42 and 44 and the offset positioning of the partial loops 50 and 56 will more easily conform to the size or shape of the body vessel in which the device is implanted.

Referring now to FIG. 2A, the first half frame 42 and second half frame 44 are shown in a collapsed, delivery position within the restraining sheath 30. The filter element 26 and obturator 32 have been removed in this figure to better show how the first half frame 42 and second half frame 44 collapse when being delivered to the target area. As can be seen in FIG. 2A, first and second control arms and partial loop forming the half frames actually define a single, complete loop which extends in a longitudinal fashion within the restraining sheath 30. Once the restraining sheath 30 has been retracted, the self-expanding properties of the material used to manufacture the first and second half frames 42 and 44 allow the partial loops to radially expand outward to the deployed position shown in FIG. 2C. The control arms will expand radially outward to some degree as well. Once deployed, the partial loops 50 and 56 cooperatively form a complete circular loop which forms an opening the filter element 26.

Figure 3:
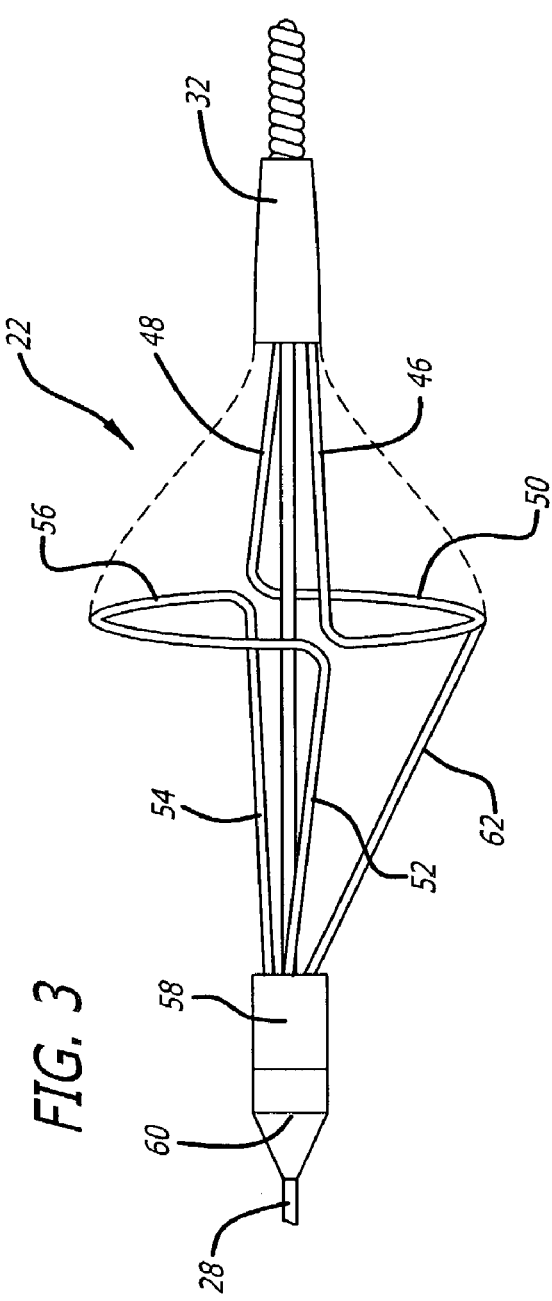
FIG. 3 is a side view of another embodiment of an embolic filtering device embodying features of the present invention.
Figure 4:
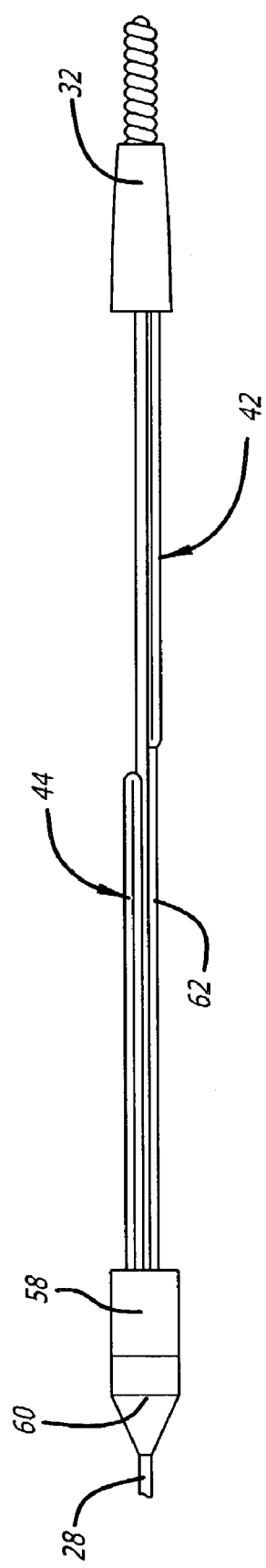
FIG. 4 is a side elevational view of the embolic filtering device of FIG. 3 in a collapsed delivery position.

Referring now to FIGS. 3 and 4, an alternative embodiment of an expandable frame 24 of the embolic filtering assembly 22 is shown. In this particular embodiment, the frame 24 includes a first half frame 42 and a second half frame 44 which cooperatively form the means for deploying the filter element of the embolic filtering assembly 22. In FIG. 3, the filter element 26 has been removed in order to better show the first half frame 42 and the second half frame 44. Dotted lines are utilized to indicate the approximate positioning of a filter element 26 with respect to the frame 24. As can best be seen in FIG. 3, the first half frame 42 is not attached to the collar 58, as is the embodiment of FIGS. 1A–1C, but rather, is placed distally away from the second half frame 44. The first half frame 42 includes a first control arm 46 and a second control arm 48 with a partial loop 50 connecting the control arms together. The opposite ends of the first and second control arms 46 and 48 are attached to a second junction or collar (not shown) which would be rotatively mounted onto the guide wire 28 to allow that half frame to move between the deployed and collapsed positions. In this regard, the ends of the first and second control arms 46 and 48 can be coupled to the guide wire by a collar which is slidably disposed over the guide wire. This collar, in turn, could be encapsulated by the obturator 32 to create a smooth tapered distal end for the filter to the embolic filtering assembly 22 to prevent trauma to the vessel walls as the device is being placed in the patient's vasculature.

The second half frame 44 is attached to the collar 58 in a similar fashion as is shown in the embodiment of FIGS. 1A–1C. This second half frame 44 also includes a first control arm 52 and a second control arm 54 connected by a partial loop 56 which extends radially outward once the frame 24 is placed in the expanded or deployed position. The first half frame 42 further includes a third control arm 62 attached to the partial loop 50 and to the collar 58 to permit the half frame 42 to be collapsed by a restraining sheath once the device is to be removed from the patient's vasculature. Without a third control arm 62 or other similar means for retracting the first half frame 42, it would be difficult for the restraining sheath to extend over the first half frame to collapse it for removal from the patient's vasculature. Preferably, the third control arm 62 is attached near the outermost periphery of the partial loop 50 to assist in the retraction of the device for removal from the patient.

FIG. 4 shows the frame 24 in its collapsed position (without restraining sheath and filter element). As can be seen in FIG. 4, the third control arm 62 extends substantially along the longitudinal length of the second half frame 44 when collapsed but will not hinder the ability of the first half frame 42 to expand radially. Again, the partial loops 50 and 56 cooperatively form a composite loop having a large opening for maintaining the filter element in a deployed position within body vessel. It should be appreciated that additional control arms could be attached to the partial loop 50, if desired.

Referring now to FIGS. 5–7, another alternative embodiment of the frame 24 which forms the embolic filtering assembly 22 is shown. As can be best seen in FIG. 5, the frame 24 again includes a first half frame 42 and a second half frame 44, which is disposed next to each other in the deployed position. Again, the filter element associated with the embolic filtering assembly 22 has been removed to better show the structure of the wire frame 24 and dotted lines are utilized to indicate the general placement of the filter element with respect to the wire frame.

The first half frame 42 includes a first control arm 46 and a second control arm 48 which are substantially the same length with the partial loop 50 connecting the first and second control arms 46 and 48 together. Likewise, the second half frame 44 includes first and second control arms of 52 and 54 with a partial loop 56 connecting the arms together. However, the size of the partial loop 50 and the partial loop 56 on the second half frame are not of equal size and shape. As is best seen in FIG. 6A, which shows an end cross-sectional view of the first and second half frames 42 and 44 when placed within a body vessel 34, the size and shape of the partial loop 50 is much larger than the second partial loop 56 of the second half frame 44. This allows for increased flexibility when the embolic filtering device is placed in body vessels of different sizes since the combination of a smaller half frame with a larger half frame allows the partial loops to crossover or overlap themselves when placed in a smaller diameter body vessel. This overlapping of the half frames still achieves and maintains a substantially circular opening for the filter element and provides proper wall apposition once deployed in the body vessel.

Referring specifically now to FIG. 6C, the advantage of using different size partial loops to form the first and second half frames is illustrated. As is shown in FIG. 6C, the partial loop 56 on the second half frame 44 can have a varying degree of arc which forms the size and shape of the loop. In FIG. 6C, an arrow indicates the range in which the arc of the partial loop 56 can be designed. Again, the partial loops on each of the first and second half frames are generally measured from the control arms and the portion of the half frame in which the partial loop begins to bend in a radial fashion once deployed. The arc of the partial loop is designated θ in FIG. 6C, and can vary from about 180° to as small as about 90°. In this regard, the size of the arc of the partial loop on the other half frame must appropriately be larger than 180° to compensate for the smaller size partial loop on the corresponding half frame. In this manner, the two partial loops 50 and 56 still cooperate to form a substantially circular opening onto which the wire element is attached. Thus, there is little chance of creating a gap between the filter element and the wall of the body vessel once the device is employed.

FIG. 6B shows an end view, partially in cross-section, of the first and second half frames 40 and 42 positioned within a smaller diameter body vessel than is shown in FIG. 6A. As can be seen in FIG. 6B, the second half frame 44 extends downward once positioned in the smaller diameter vessel to allow the partial loops 50 and 56 to overlap to complete the circular opening needed for the filter element.

Referring now to FIGS. 8–10, another embodiment of the frame 24 is shown. In this particular set of figures, only a single half frame 42 is shown for purposes of clarity. Additionally, the filter element 26 is again shown with dotted lines to indicate the general location of the filter with respect to this half frame 42. As can best be seen in FIGS. 8 and 9, this half frame 42 includes a specially shaped first control arm 46 and second control arm 48. The particular length and shape of these two control arms 46 and 48 differ to allow these two elements to be withdrawn and collapsed at different times as the restraining sheath 30 (shown in FIG. 9) begins to collapse the half frame. As best can be seen in FIG. 8, as the first control arm 46 extends distally away from the collar 58, it extends outwardly in a more radial fashion than does the second control arm 46. Arrows utilized in FIG. 8 show the difference in the length (designated x) at which point both control arms begin to extend radially outward once placed in the deployed position. In this regard, the first control arm 46 transitions from its connection point at junction 58 sooner than does the transition point on the second control arm 48. As a result, as the restraining sheath 30 is retracted over the half frame 42, the first control arm 46 comes in contact with the end 64 of the retracting sheath 30 sooner than the second control arm 46. Eventually, the end 64 of the restraining sheath will contact the second control arm 46, however, at that point, a substantial length of the first control arm 44 has already been collapsed back to the delivery position within the lumen of the restraining sheath. As a result of this staggered arrangement of control arms, the restraining sheath does not have to initially impart as large a collapsing force on the first and second control arms simultaneously, thus making it easier to retract the half frame 42 into the lumen of the restraining sheath.

FIG. 10 shows the half frame 42 placed in its collapsed, delivery position as it is delivering advanced into the target area or after the filter has been retrieved following the interventional procedure. Again, FIG. 10 shows only one of the two half frames and the filter element has been moved to better show the half frame in its collapsed position. The second half frame can have similarly staggered control arms as well.

A further variation of the expandable frame shown and described above can be seen in FIGS. 11 and 12. In this particular embodiment, the cage 24 includes a first half frame 42 having a pair of control arm 46 and 48 that are substantially the same length. A partial loop 50 connects the ends of the control arms together. The second half frame 44, on the other hand, includes first and second control arms 52 and 54 which are essentially the same length, but are shorter than the length of the control arms 46 and 48 of the first half frame 42. In this regard, the arrow A in FIG. 12 shows the length of the first and second control arms 46 and 48, while arrow B shows the shorter length of the first and second control arms of 52 and 54 of the second half frame. The difference in the length of the control arms is indicated by the numeral C in FIG. 12. In this particular embodiment of the expandable frame 24, the shorter lengths of the control arms of this second half frame are useful whenever the embolic filtering assembly is deployed, for example, in a curved section of the body vessel. In this regard, the shorter control arms of the second half-basket would be deployed along the shorter radius of the curved body vessel with the longer control arms of the first half frame 42 being deployed along the larger radius curvature of the body vessel. Accordingly, the difference in length (c) between the deployed partial loops of the first and second half frames will shorten when deployed on a curved body vessel. As a result, the partial loops will be maintained closer together once deployed to maintain correct wall apposition between filter element and the body vessel.

In the embodiment shown in FIGS. 11 and 12, the outward-most length (radius) of the partial loop 50 of the first half frame 42 can be larger than the outermost length (radius) of the partial loop forming the second half frame 44. In FIG. 12, radius of the partial loop 50 is designated by arrow D. Arrow E shows the shorter radius of the partial loop 56 which forms part of the second half frame 44. This shorter radius partial loop 56 may be easier to be positioned within a curved body vessel. The composite loop formed by the partial loops of the two half baskets can thus be better positioned and more conformable with the size and shape of the curved body vessel. It should be appreciated that the radius of the various partial loops shown in the previously described embodiments can be varied as well. Also, the radius of the partial loop on each half frame could be substantially identical as is shown in the embodiments of FIGS. 1A and 3.

Referring now to FIGS. 13–16, the cage 24 is shown including coils 66 which are wrapped around the partial loops 50 and 56 of the first and second half frames in order to increase the radiopacity of the device during fluoroscopy. The coils 66 are generally made from a material, such as gold or platinum, which provides additional radiopacity during fluoroscopy. It should be noted that materials which could be utilized in forming the half frames includes nickel-titanium or Nitinol, which generally has poor visibility under fluoroscopy. Therefore, the placement of highly visible coils 66 on the partial loops 50 and 56 of the first and second half cages enhances the physician's ability to visualize the device once implanted in the patient's vasculature. FIGS. 14 and 16 show one of the problems which can be caused by placement of a radiopaque coil along the partial loop of the half frame. Basically, the problem with placing radiopaque coils on the device stems from the fact that the winding of the coils sometimes hinder the ability of the partial loop to collapse to a small profile. As is shown in FIG. 16, the outermost radius of the partial loop beings to bow outwardly when collapsed due to the presence of the radiopaque coil 66. The stiffness of the radiopaque coil can cause the radius of the bend in the partial loop area to be relatively large, which further increases the collapse profile of the two half frames.

One method for reducing this stiffness, and for decreasing the crossing profile, is to remove some of the windings of the radiopaque coil from the area of the bend. In FIG. 15, the reason that the collapsed radius at the end of the partial loop is reduced is due to the reduction of the numbers of windings of the radiopaque coil. It should be remembered that this coil 66, much like a spring, can only compress until the coils touch one another, which limits the size that the radius can be reduced to. Another way to solve this problem or reduce the propensity for it is to increase the pitch of the entire coil or locally at the location of the bend of the partial loop.

Referring now to FIGS. 17–20, the frame 24 is shown having a region of articulation 68 formed preferably at the partial loop of the half frames used to construct the frame 24. First, as can be seen in FIG. 17, the region of articulation 68 is shown as a single loop formed at a location on the partial loop which aids the collapsing and deployment of the half frame. This region of articulation 68, shown in an exploded view in FIGS. 18A and 18B, can be configured either as a loop which extends proximately from the partial loop, as is shown in FIG. 18A, or distally of the partial loop, as is shown in FIG. 18B. Although the regional articulation 68 is shown in the middle of the partial loop 50, it could be located at any location along the length of the partial loop 50. Referring specifically now to FIG. 19, the region of articulation 68 does not have to be a complete loop formed within the partial loop 50, but rather can be D-shaped loop which extends either proximal to the partial loop 50, as is shown in FIG. 20A, or distal to the partial loop 50, as is shown in FIG. 20B.

Figure 21:
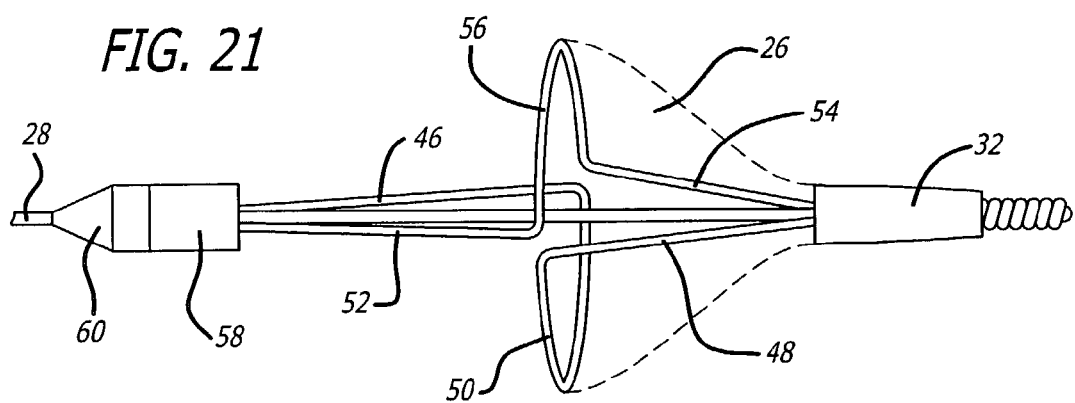
FIG. 21 is a side view of another embodiment of an embolic filtering device embodying features of the present invention.
Figure 22:
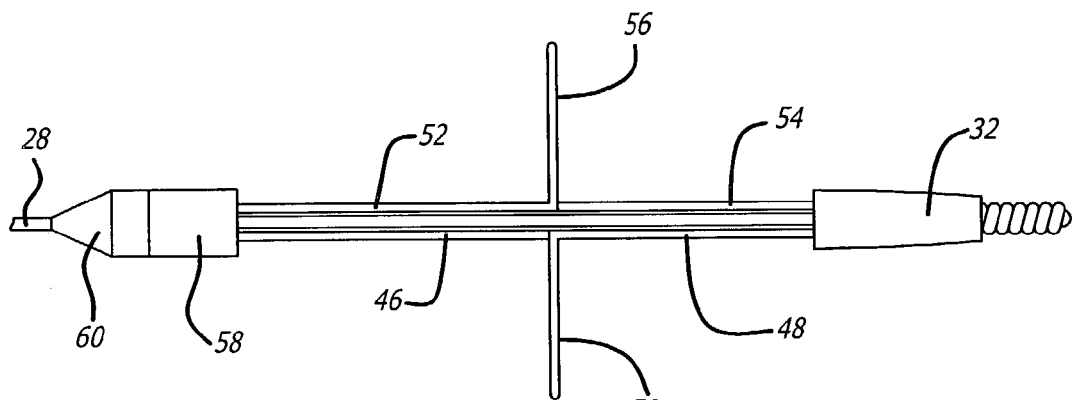
FIG. 22 is a side elevational view of the embolic filtering device of FIG. 21 in its expanded, deployed position.

Referring now to FIGS. 21 and 22, an alternative embodiment of the expandable frame 24 is shown. In this particular embodiment, the frame 24 includes a first half frame 42 having a first control arm 46 connected to a partial loop 50 and a second control arm 48 which extends distally from the partial loop. In this embodiment, at the first and second control arms 46 and 48 are not adjacent to each other, as is shown in the previously described embodiments of the half frames. Likewise, the second half frame 44 includes a first control arm 52 connected to partial loop 56 and a second control arm 54 which also extends distally from the partial loop 56. As can be seen in FIG. 21, the ends of the second control arms are attached to a collar (not shown) which is covered by the obturator 32 shown in FIGS. 21 and 22. It should be appreciated that although the first and second control arms are shown substantially of equal length, it is possible to make this set of control arms smaller than the other set, if desired, to create a particular embodiment for particular use in a patient's vasculature. Additionally, the radius and arc of the partial loops 50 and 56 can be approximately the same, as is shown in FIGS. 21 and 22, or the radius and arc can be of differing sizes to accommodate the filtering device when implanted in, for example, curved body vessels.

Figure 23:
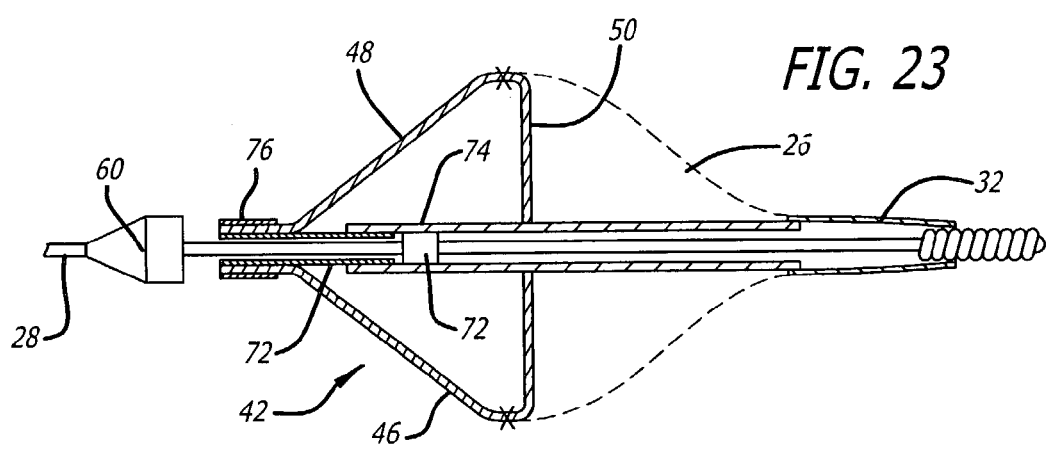
FIG. 23 is a side elevational view, partially in cross-section, of another embodiment of an embolic filtering device embodying features of the present invention.

There is still another alternate embodiment of the embolic filtering assembly 22 shown in FIG. 23. In this particular embodiment, the half frame 42 (only one of which is shown in FIG. 23) is mounted onto an inner sleeve member 70 which is disposed on the guide wire 28 between a pair of stop fittings 60 and 72. A second tubular member 74 attaches to the distal end of this inner sleeve 70 which extends to the proximal end of the obturator 32. As can be seen in FIG. 26, the tubular structure formed by the inner sleeve 70 and the tubular member allow the embolic filtering assembly 22 to rotate on the guide wire and helps to prevent the filter element 26 from twisting relative to the expandable frame. The outer sleeve 76 is connected to the ends of the control arms 46 and 48 of the half frame 42 in order to mount it onto this composite tubular assembly. As can be seen in FIG. 23, the filter element 26, indicated by dotted lines, extends from the partial loops of the half frames forming the collapsible frame to the obturator 32 where it can be bonded, for example, by adhesive or by heat. In this regard, the present embodiment of the embolic filtering assembly helps to prevent the filter from twisting relative to the expandable frame and prevents the distal end of the filter element from moving proximal. The first and second half frames which form the expandable frame 24 can be coupled together as the locations marked by x's in FIG. 23 to prevent overlapping of the half frames in smaller diameter vessels. The first and second half frames of the other embodiments described herein could also be coupled together to prevent overlapping of the half frames during use. Alternatively, sleeve 70 can be a tapered coil or tapered tubing which could match the core grind of the guide wire. The inner sleeve member could also have a step or constant step low slant instead of a tapered profile to eliminate material to allow for a smaller collapsed profile. The materials to be used to form the tubular member 74 could be hypotube made from stainless steel or a superelastic material such as nickel-titanium. This allows the tubular member 74 to be more flexible while still maintaining proper torque transmission from the proximal end of the guide wire to the distal end of the wire. It should be appreciated that this inner tubular structure could also be implemented with any of the other embodiments of the collapsible frame 24 described above and shown in the accompanying figures.

The expandable frame of the present invention can be made in many ways. One way is to use a wire made from a material possessing self-expanding properties. The wire can be set to the desired size and shape when placed in the expanded position. Another particular method of making the basket is to cut a thin-walled tubular member, such as nickel-titanium hypotube, to remove portions of the tubing in the desired pattern for each half frame, leaving relatively untouched the portions of the tubing which are to form the control arms and partial loop. The tubing may be cut into the desired pattern by means of a machine-controlled laser. Prior to laser cutting the pattern, the tubular member could be formed with varying wall thicknesses which can be used to create flexing portions on the half frames.

The tubing or wire used to make the half frames could possible be made of suitable biocompatible material such as spring steel. Elgiloy is another material which could possibly be used to manufacture the half frames. Also, very elastic polymers could be used to manufacture the half frames.

The size is often very small, so the wire or tubing from which the half frames and made must necessarily have a small diameter. Typically, the tubing has an outer diameter on the order of about 0.020–0.040 inches in the unexpanded condition. The wall thickness of the tubing is usually about 0.076 mm (0.003–0.006 inches). As can be appreciated, the width at the bending points of the articulation regions will be less. For frames implanted in body lumens, such as PTA applications, the dimensions of the tubing maybe correspondingly larger.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished frame. The frame can be laser cut much like a stent is laser cut. Details on how the tubing can be cut by a laser are found in U.S. Pat. No. 5,759,192 (Saunders), U.S. Pat. No. 5,780,807 (Saunders) and U.S. Pat. No. 6,131,266 (Saunders) which have been assigned to Advanced Cardiovascular Systems, Inc.

The process of cutting a pattern for the frame into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

A suitable composition of nickel-titanium which can be used to manufacture the strut assembly of the present invention is approximately 55% nickel and 45% titanium (by weight) with trace amounts of other elements making up about 0.5% of the composition. The austenite transformation temperature is between about 0° C. and 20° C. in order to achieve superelasticity. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is approximately 0.5%. The breaking elongation is a minimum of 10%. It should be appreciated that other compositions of nickel-titanium can be utilized, as can other self-expanding alloys, to obtain the same features of a self-expanding frame made in accordance with the present invention.

In one example, the frame of the present invention can be laser cut from a tube of nickel-titanium (Nitinol) whose transformation temperature is below body temperature. After the pattern of each half frame is cut into the hypotube, the tubing is expanded and heat treated to be stable at the desired final diameter. Alternatively, the half frames can be made from Nitinol wire with the shape of the half frames being set via known techniques well-known in the art. The heat treatment also controls the transformation temperature of the basket such that it is super elastic at body temperature. The transformation temperature is at or below body temperature so that the basket is superelastic at body temperature. The frame is usually implanted into the target vessel which is smaller than the diameter of the frame in the expanded position so that the control arms apply a force to the vessel wall to maintain the frame in its expanded position. It should be appreciated that the frame can be made from either superelastic, stress-induced martensite NiTi or shape-memory NiTi.

Another way of making the frame of the present device is to utilize a shape-memory material, such as nickel-titanium, which has the half frames cut utilizing a machine-controlled laser. A tubular piece of material or wire could be utilized in this process. The frame could be manufactured to remain in its open position while at body temperature and would move to its unexpended position upon application of a low temperature. One suitable method to allow the frame to assume a change phase which would facilitate the frame and filter element being mounted into the restraining sheath include chilling the filter assembly in a cooling chamber maintained at a temperature below the martensite finish temperature through the use of liquid nitrogen. Once the frame is placed in its collapsed state, the restraining sheath can be placed over the frame to prevent the frame from expanding once the temperature is brought up to body temperature. Thereafter, once the filtering device is to be utilized, the restraining sheath is simply retracted to allow the basket to move to its expanded position within the patient's vasculature. If super elastic NiTi is used, the frame/filter assembly can be simply back loaded into the restraining sheath. The frame would be "set" to the expanded position.

The frame could also be manufactured by laser cutting a large diameter tubing of nickel-titanium which would create the two half frames in its expanded position. Thereafter, the frame could be placed in its unexpanded position by backloading the frame into a restraining sheath which will keep the device in the unexpanded position until it is ready for use. If the frame is formed in this manner, there would be no need to heat treat the tubing to achieve the final desired diameter. This process of forming the frame could be implemented when using superelastic nickel-titanium or shape-memory nickel-titanium.

The polymeric material which can be utilized to create the filtering element include, but is not limited to, polyurethane and Gortex, a commercially available material. Other possible suitable materials include ePTFE. The material can be elastic or non-elastic. The wall thickness of the filtering element can be about 0.00050–0.0050 inches. The wall thickness may vary depending on the particular material selected. The material can be made into a cone or similar shape utilizing blow-mold or dip-mold technology. The openings can be any different shape or size. A laser, a heated rod or other process can be utilized to create perfusion openings in the filter material. The holes, would of course be properly sized to catch the particular size of embolic debris of interest. Holes can be lazed in a spiral pattern with some similar pattern which will aid in the re-wrapping of the media during closure of the vice. Additionally, the filter material can have a "set" put in it much like the "set" used in dilatation balloons to make the filter element re-wrap more easily when placed in the collapsed position.

The materials which can be utilized for the restraining sheath can be made from polymeric material such as crosslinked HDPE. This sheath can alternatively be made from a material such as polyolifin which has sufficient strength to hold the compressed filter assembly and has relatively low frictional characteristics to minimize any friction between the filtering assembly and the sheath. Friction can be further reduced by applying a coat of silicone lubricant, such as Microglide®, to the inside surface of the restraining sheath before the sheaths are placed over the filtering assembly.

Further modifications and improvements may additionally be made to the device and method disclosed herein without departing from the scope of the present invention. Accordingly, it is not intended that the invention be limited, except as by the appended claims.

What is claimed is:

1. An embolic filtering device used to capture embolic debris in a body vessel, comprising:
    a guide wire having a proximal end and a distal end;
    an expandable filter assembly including a self-expanding frame having a first half frame adapted to move between an unexpanded position and an expanded position, the first half frame having a first control arm connected to a second control arm by a partial loop; a second half frame adapted to move between an unexpanded position and an expanded position, the second half frame having a first control arm connected to a second control arm by a partial loop, the partial loops of the first and second half frames cooperating to form a composite opening, the first control arm of the first half frame being disposed substantially adjacent to the second control arm of the first half frame and first control arm of the second half frame being disposed substantially adjacent to the second control arm of the second half frame;
    a filtering element attached to the partial loops of the first and second half frames; and
    means for rotatably mounting the expandable filter assembly to the guide wire.

2. The expandable frame of claim 1, wherein the first control arm of the first half frame is smaller than the second control arm of the first half frame and the first control arm of the second half frame is smaller than the second control arm of the second half frame.

3. The expandable frame of claim 2, wherein the partial loops of the first and second half frame each have a particular radius, wherein one of the partials loops has a smaller radius than the other partial loop.

4. The embolic filtering device of claim 1, wherein the first control arm of the second half frame is smaller than the second control arm of the second half frame.

5. The embolic filtering device of claim 1, wherein the second control arm of the second half frame is smaller than the first control arm of the second half frame.

6. An embolic filtering device used to capture embolic debris in a body vessel, comprising:
    an elongate member having a proximal end and a distal end;
    a filter assembly associated with the elongate member, the filter assembly including:
    a first half frame adapted to move between an unexpanded position and an expanded position, the first half frame having a first control arm connected to a second control arm by a partial loop;
    a second half frame adapted to move between an unexpanded position and an expanded position, the second half frame having a first control arm connected to a second control arm by a partial loop, the partial loops of the first and second half frames cooperating to form a composite opening for attachment of a filtering element when placed in the expanded position; and
    a filtering element attached to the partial loops of the first and second half frames;
    wherein the first control arm of the first half frame is smaller than the second control arm of the first half frame and the first control arm of the first half frame is disposed substantially adjacent to the second control arm of the first half frame and first control arm of the second half frame is disposed substantially adjacent to the second control arm of the second half frame.

7. The embolic filtering device of claim 6, wherein the first control arm of the second half frame is smaller than the second control arm of the second half frame.

8. The embolic filtering device of claim 6, wherein the second control arm of the second half frame is smaller than the first control arm of the second half frame.

9. The embolic filtering device of claim 6, wherein the partial loops of the first and second half frame each have a particular radius, wherein one of the partials loops has a smaller radius than the other partial loop.

10. The embolic filtering device of claim 6, wherein the elongate member is a guide wire.

11. The embolic filtering device of claim 6, wherein the filter assembly is rotatable mounted to the elongate member.

12. The embolic filtering device of claim 6, wherein the elongate member is a guide wire.

13. The embolic filtering device of claim 6, wherein the filter assembly is rotatable mounted to the elongate member.

14. An embolic filtering device used to capture embolic debris in a body vessel, comprising:
   a guide wire;
   a filter assembly rotatably attached to the guide wire, the filter assembly including:
   a first half frame adapted to move between an unexpanded position and an expanded position, the first half frame having a first control arm connected to a second control arm by a partial loop;
   a second half frame adapted to move between an unexpanded position and an expanded position, the second half frame having a first control arm connected to a second control arm by a partial loop;
   a second half frame adapted to move between an unexpanded position and an expanded position, the second half frame having a first control arm connected to a second control arm by a partial loop, the partial loops of the first and second half frames cooperating to form a composite opening for attachment of a filtering element when placed in the expanded position; and
   a filtering element attached to the partial loops of the first and second half frames,
   wherein the first control arm of the first half frame is smaller than the second control arm of the first half frame and the first control arm of the second half frame is smaller than the second control arm of the second half frame and the first control arm of the first half frame is disposed substantially adjacent to the second control arm of the first half frame and first control arm of the second half frame is disposed substantially adjacent to the second control arm of the second half frame.

15. An embolic filtering device used to capture embolic debris in a body vessel, comprising:
   a guide wire having a proximal end and a distal end;
   an expandable filter assembly having a proximal end and a distal end, the filter assembly including a self-expanding frame having a first half frame adapted to move between an unexpanded position and an expanded position, the first half frame having a first control arm connected to a second control arm by a partial loop; a second half frame adapted to move between an unexpanded position and an expanded position, the second half frame having a first control arm connected to a second control arm by a partial loop, the partial loops of the first and second half frames cooperating to form a composite opening, the first control arm of the first half frame being disposed substantially adjacent to the second control arm of the first half frame and first control arm of the second half frame being disposed substantially adjacent to the second control arm of the second half frame;
   a filtering element attached to the partial loops of the first and second half frames; and
   means for rotatably mounting the expandable filter assembly to the guide wire; wherein one of the proximal end and distal end of the filter assembly is prevented from longitudinal movement along the guide wire.

* * * * *

UNITED STATES PATENT AND TRADEMARK OFFICE
CERTIFICATE OF CORRECTION

PATENT NO. : 7,252,675 B2  Page 1 of 1
APPLICATION NO. : 10/260710
DATED : August 7, 2007
INVENTOR(S) : Andy E. Denison et al.

It is certified that error appears in the above-identified patent and that said Letters Patent is hereby corrected as shown below:

Title Page, U.S. PATENT DOCUMENTS, insert --6,051,015   4/2000   Maahs--.

Column 4,
Line 45, delete "unexpended" and insert --unexpanded--.

Column 5,
Line 17, delete "In aspect" and insert --In one aspect--.
Line 54, delete "that the event" and insert --the event--.

Column 14,
Line 36, delete "proximately" and insert --proximally--.

Column 15,
Line 62, delete "possible" and insert --possibly--.
Line 67, delete "and" and insert --are--.

Column 17,
Line 10, delete "unexpended" and insert --unexpanded--.
Line 59, delete "polyolifin" and insert --polyolefin--.

Column 19,
Line 11, delete "partials loops" and insert --partial loops--.
Lines 30 through 33, delete.

Signed and Sealed this

Eleventh Day of March, 2008

JON W. DUDAS
*Director of the United States Patent and Trademark Office*